United States Patent
Lo et al.

(10) Patent No.: US 11,610,666 B2
(45) Date of Patent: *Mar. 21, 2023

(54) SYSTEMS AND METHODS OF MANAGING TREATMENT OF A CHRONIC CONDITION BY SYMPTOM TRACKING

(71) Applicant: CORCEPT THERAPEUTICS, INC., Menlo Park, CA (US)

(72) Inventors: Steven Lo, Menlo Park, CA (US); David Penake, Menlo Park, CA (US); John Lyons, Menlo Park, CA (US); Lisa Saginian, Menlo Park, CA (US)

(73) Assignee: Corcept Therapeutics, Inc., Menlo Park, CA (US)

(*) Notice: Subject to any disclaimer, the term of this patent is extended or adjusted under 35 U.S.C. 154(b) by 824 days.

This patent is subject to a terminal disclaimer.

(21) Appl. No.: 15/954,262

(22) Filed: Apr. 16, 2018

(65) Prior Publication Data

US 2018/0240544 A1    Aug. 23, 2018

Related U.S. Application Data

(63) Continuation of application No. 14/715,311, filed on May 18, 2015, now Pat. No. 9,977,875.
(Continued)

(51) Int. Cl.
*G16H 30/40* (2018.01)
*A61K 31/567* (2006.01)
(Continued)

(52) U.S. Cl.
CPC .......... *G16H 30/40* (2018.01); *A61B 5/1079* (2013.01); *A61K 31/567* (2013.01);
(Continued)

(58) Field of Classification Search
CPC .... G06V 40/16; G06V 40/165; A61B 5/1079; G06T 2207/30196; G06T 2207/30201
See application file for complete search history.

(56) References Cited

U.S. PATENT DOCUMENTS

2004/0030225 A1    2/2004  Nunome
2005/0283385 A1   12/2005  Hunkeler et al.
(Continued)

FOREIGN PATENT DOCUMENTS

CN    101283918 A    10/2008
CN    102063579 A     5/2011
(Continued)

OTHER PUBLICATIONS

Kosilek, R. P., Schopohl, J., Grunke, M., Reincke, M., Dimopoulou, C., Stalla, G. K., . . . & Schneider, H. J. (2013). Automatic face classification of Cushing's syndrome in women—a novel screening approach. Experimental and Clinical Endocrinology & Diabetes, 121(09), 561-564. (Year: 2013).*
(Continued)

*Primary Examiner* — Jesse P Frumkin
(74) *Attorney, Agent, or Firm* — Kilpatrick Townsend & Stockton LLP

(57) ABSTRACT

Devices, systems, and methods for use in managing treatment of a chronic disorder with pharmaceutical or therapeutic compounds by tracking symptoms associated with the disorder. Methods include inputting patient attributes, factors and various and other data relating to the patient in conjunction with one or more symptoms into a symptom tracking system and outputting a report of the data tracked over time to any of the patient, a medical professional and a drug developer to improve identification of a relapse of the chronic condition and improve management of the treatment regimen for any and all patients.

21 Claims, 23 Drawing Sheets

Patient Photo Timeline

Related U.S. Application Data

(60) Provisional application No. 61/994,815, filed on May 16, 2014.

(51) Int. Cl.
| | | |
|---|---|---|
| *G01N 33/49* | (2006.01) | |
| *G16H 50/20* | (2018.01) | |
| *G06V 40/16* | (2022.01) | |
| *A61B 5/107* | (2006.01) | |
| *G06T 7/60* | (2017.01) | |
| *G16H 15/00* | (2018.01) | |
| *A61P 5/46* | (2006.01) | |
| *G16Z 99/00* | (2019.01) | |

(52) U.S. Cl.
CPC ............. *G01N 33/492* (2013.01); *G06T 7/60* (2013.01); *G06V 40/16* (2022.01); *G16H 15/00* (2018.01); *G16H 50/20* (2018.01); *G16Z 99/00* (2019.02); *A61P 5/46* (2018.01)

(56) References Cited

U.S. PATENT DOCUMENTS

| | | |
|---|---|---|
| 2006/0036619 A1 | 2/2006 | Fuerst et al. |
| 2008/0242977 A1 | 10/2008 | Sirohey et al. |
| 2010/0169409 A1 | 7/2010 | Fallon et al. |
| 2011/0224179 A1 | 9/2011 | Newell-Price et al. |
| 2013/0131030 A1 | 5/2013 | Belanoff et al. |
| 2013/0144676 A1 | 6/2013 | O'Sullivan et al. |
| 2013/0282404 A1 | 10/2013 | Janevski et al. |
| 2015/0088540 A1 | 3/2015 | Lo et al. |
| 2015/0332020 A1 | 11/2015 | Lo et al. |

FOREIGN PATENT DOCUMENTS

| | | |
|---|---|---|
| CN | 102231172 A | 11/2011 |
| CN | 103324853 A | 9/2013 |
| CN | 103690149 | 4/2014 |
| JP | 2008210399 A | 9/2008 |
| JP | 2014503913 A | 2/2014 |
| WO | 2014028888 A2 | 2/2014 |
| WO | 2015176062 | 11/2015 |

OTHER PUBLICATIONS

CN201580037068.X , "Office Action", dated Mar. 26, 2020, 22 pages.

Boehringer et al., "Automated Syndrome Detection in a Set of Clinical Facial Photographs", American Journal of Medical Genetics Part A, vol. 155, No. 9, Sep. 1, 2011, pp. 2161-2169.

Cushing syndrome definition, Mayo Clinic, retrieved online Jul. 13, 2015, at http://www.mayoclinic.org/diseases-conditions/cushing-syndrome/basics/definition/con-20032115?reDate=13072015 (3 pages).

Cushing disease definition, MedlinePlus Medical Encyclopedia, retrieved online Jul. 13, 2015, at http://www.nlm.nih.gov/medlineplus/ency/article/000348.htm (5 pages).

EP15793415.9 , "Extended European Search Report", dated Jan. 2, 2018, 11 pages.

PCT/US2015/031408 , "International Preliminary Report on Patentability", dated Dec. 1, 2016, 8 pages.

PCT/US2015/031408 , "International Search Report and written opinion", dated Oct. 30, 2015, 12 pages.

PCT/US2015/031408 , "Invitation to Pay Add'l Fees and Partial Search Report", dated Aug. 14, 2015, 2 pages.

CN201580037068.X , "Office Action", dated Mar. 26, 2020, 10 pages.

EP15793415.9 , "Office Action", dated Nov. 8, 2019, 10 pages.

JP2016-56772 , "Office Action", dated Aug. 6, 2019, 14 pages.

Nakaikenji, "FDA wa mifepurisuton wo naiinseikusshingushokogun ni ninka (FDA approved mifepristone for endogenous Cushing's syndrome)", Available online at, <URL:blog.livedoor.jp/nakaikeiji/archives/51923385.html> retrieved on Jul. 30, 2019, Feb. 19, 2012).

\* cited by examiner

SYSTEMS AND METHODS OF MANAGING TREATMENT OF A CHRONIC CONDITION BY SYMPTOM TRACKING

CROSS-REFERENCES TO RELATED APPLICATIONS

This application is a Continuation of U.S. Non-Provisional patent application Ser. No. 14/715,311, filed May 18, 2015, and claims priority to U.S. Provisional Patent Application No. 61/994,815, filed May 16, 2014, the entire contents of which are incorporated herein by reference.

BACKGROUND OF THE INVENTION

The present invention generally pertains to management of chronic conditions, in particular chronic conditions that are treated utilizing administration of pharmaceutical or other therapeutic compounds.

While medical treatments utilizing administration of pharmaceutical or therapeutics are widespread, the effectiveness of a given treatment may vary widely from patient to patient, particularly when administered over a long period of time for treatment of a chronic condition. Even when the efficacy of a given treatment has a high degree of predictability in most patients, the success of treatment may still vary considerably based on the patient's compliance with the prescribed treatment as well as the ability of the physician to prescribe an appropriate treatment regimen for a given patient. In addition, certain chronic conditions may vary in intensity over time and patients may experience occasional relapse or an increase in symptoms that require changes in treatment. It can often be difficult to recognize these periods of relapse or increase in symptoms before their effects are full-blown causing escalating symptoms or prolonged periods of relapse unnecessarily. These difficulties can become even more problematic when the effect of a treatment and associated pharmaceutical or therapeutic is less predictable, or vary considerably between patients.

Given the complexities and challenges posed by conventional treatments utilizing administration of pharmaceuticals, there exists a need to improve treatment management of chronic conditions. There further exists a need to provide a means to prevent relapse of the chronic condition.

BRIEF SUMMARY OF THE INVENTION

The present invention generally pertains to management of chronic conditions, particularly those conditions treated by administration of pharmaceutical or other therapeutic compounds. In particular, the invention pertains to tracking of one or more symptoms associated with a chronic condition to facilitate identification of changes in symptoms to improve management of the chronic condition being treated, prevent relapse and improve patient outcomes.

BRIEF DESCRIPTION OF THE DRAWINGS

FIGS. 6A-6C illustrate a screenshot of an example symptom tracking system for management of a chronic condition relating to tracking of patient symptoms over time and establishing a baseline and goal to assess progress.

DETAILED DESCRIPTION OF THE INVENTION

Figure 1:
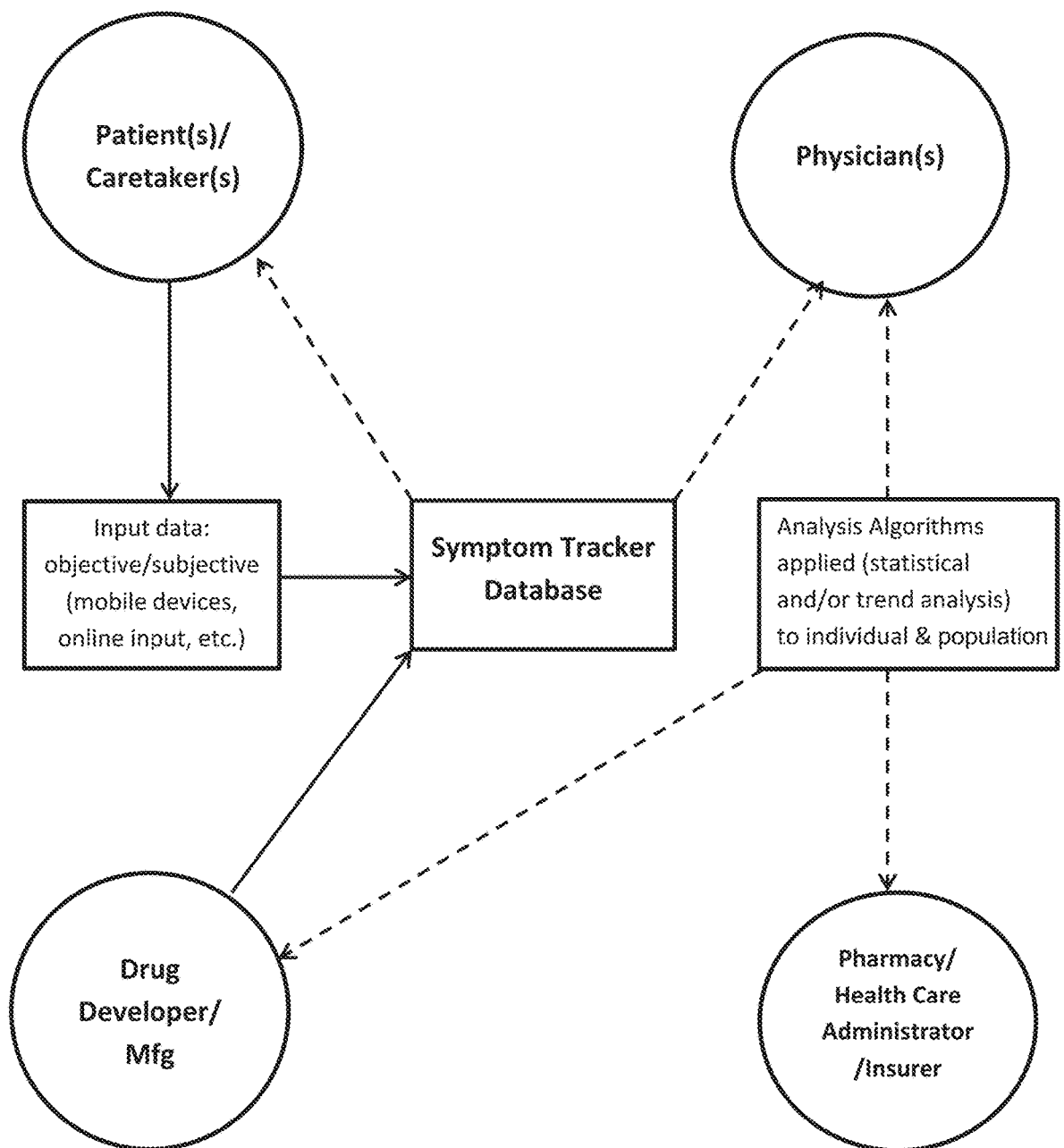
FIG. 1 illustrates a graphical system overview of example embodiment of the invention.

The present invention generally provides a system for use in managing chronic conditions, in particular, conditions treated with one or more drugs or therapeutic compounds. In certain aspects, the system provides a symptom tracking information management system (e.g. database and the like) in which attributes relating to a patient having the chronic condition and symptoms of the patient are received and tracked over time to facilitate monitoring of the condition and an associated treatment regimen. Such information may be output periodically or upon one or more symptoms exceeding a predetermined range or value to alert the patient or medical professional to a change in symptoms or condition in a particular patient that may necessitate further action. Such action may include counseling, follow-up visits, further physiological testing and/or modifications to the treatment regimen. In certain aspects, such information may be collected from multiple patients and analyzed, such as in a statistical analysis, to alert the medical professions or a drug developer to trends, correlations, or interactions between certain patient factors, symptoms and treatment regimens, which may inform and improve prescribed treatment regimens. In another aspect, methods may further include tracking of one or more factors associated with the chronic condition that are monitored independently from or in combination with tracking of associated symptoms. Such factors may include tracking of various compounds within the patient's blood, including but not limited to blood glucose, hormone levels, drug levels and the like. Tracking of one or more additional factors in combination with one or more symptoms may be further advantageous by allowing determination of a correlation between symptoms and the chronic condition and/or the one or more factors or may be used to provide verification of a likely change in the chronic condition indicated by tracked changes in patient symptoms. In some embodiments, any information entered by the patient is accessible to the patient to facilitate tracking of the condition by the patient; all or some of the information is accessible by a medical professional treating the patient; and all or some of the information is accessible to a drug developer. At least some of the information entered by the patient may remain confidential to the patient or to the patient and physician. In some aspects, the information entered by multiple patients is analyzed and output to a drug developer to provide statistical information as to the condition, symptoms and treatment based on one or more attributes of the patient (e.g. age, sex, weight, location, treating physician, treatment duration) or based on one or more attributes of the prescribed treatment regimen.

As referred to herein, the term "symptom" comprises any objective or subjective feature or sign resulting from or of any potential interest in regard to the chronic condition or illness being treated or management thereof. While classically, the term "sign" refers to test results (e.g. blood cell count) or features noticed by those other than the patient, within the context of this disclosure such signs are included within the term "symptom." Such symptoms can be identified by any of the patient, a caretaker, physician, medical professional, or anyone with sufficient exposure to the patient or samples from the patient. In addition, the term "user" refers to any user of the information system, which may include the patient, a caretaker, a medical professional, facility, insurer, pharmacy, drug developer or drug manufacturer or third party.

In one aspect, the system provides a symptom tracking information system in which one or more fields of information relating to a patient, physician and drug treatment are received by the patient and/or medical professional and information regarding one or more symptoms are entered by the patient over time (preferably at regular intervals) and output to the patient and/or physician to facilitate monitoring and assessment of the condition. Such output may be in the form of an e-mailed or printed report and may be provided periodically (e.g. weekly, monthly) or may be output in response to a condition (e.g. change in treatment or physicians, one or more symptoms exceeding a certain value or range, or a certain combination of symptoms). In one aspect, the patient inputs information regarding the one or more symptoms on a regular basis (e.g. weekly) so that a tracking of the symptoms can more accurately reflect stability of the treatment and associated symptoms or an increase in symptoms, which may be indicative of a relapse or a need to modify the treatment regimen (e.g. dosage increase).

An example of a chronic condition that can be difficult to treat is a hormonal disorder, such as Cushing's Syndrome. "Cushing syndrome occurs when your body is exposed to high levels of the hormone cortisol for a long time. The most common cause of Cushing syndrome, sometimes called hypercortisolism, is the use of oral corticosteroid medication. The condition can also occur when your body makes too much cortisol. Too much cortisol can produce some of the hallmark signs of Cushing syndrome—a fatty hump between your shoulders, a rounded face, and pink or purple stretch marks on your skin. Cushing syndrome can also result in high blood pressure, bone loss and, on occasion, diabetes. Treatments for Cushing syndrome can return your body's cortisol production to normal and noticeably improve your symptoms. The earlier treatment begins, the better your chances for recovery." see the page "diseases-conditions/cushing-syndrome/basics/definition/con-20032115" at the "mayoclinic.org" website.).

A particular form of Cushing's Syndrome is Cushing's disease. "Cushing's disease is caused by a tumor or excess growth (hyperplasia) of the pituitary gland. This gland is located at the base of the brain. People with Cushing's disease have excess ACTH, which stimulates the production and release of cortisol, a stress hormone. Too much ACTH means too much cortisol. Cortisol is normally released during stressful situations. It controls the body's use of carbohydrates, fats, and proteins and also helps reduce the immune system's response to swelling (inflammation). Treatment involves surgery to remove the pituitary tumor, if possible. After surgery, the pituitary may slowly start to work again and return to normal. During the recovery process, a patient may need cortisol replacement treatments. Radiation treatment of the pituitary gland may also be used. If the tumor does not respond to surgery or radiation, the patient may get medications to stop or decrease production of cortisol. If such treatments are not successful, the adrenal glands may be removed to stop excess levels of cortisol from being produced." see the page "medlineplus/ency/article/000348.htm" at the nlm.nih.gov" website).

Treatment of endocrine disorders, such as Cushing's Syndrome, can be particularly difficult to manage due to less predictable patient response to administration of a synthetic steroid, such as mifepristone. Mifepristone is a synthetic steroid that binds progesterone and glucocorticoid receptors and has been employed to treat a number of conditions including meningioma, uterine fibroids, hyperadrenocorticism, metabolic, oncologic, opthamalogic, central nervous system disorders and certain psychiatric illnesses. Examples of such metabolic disorders include diabetes, obesity, antipsychotic induced weight gain, hypertension, and osteoporosis; examples of oncologic illness include various types of cancers, including ovarian cancer and prostate cancer; examples of central nervous system disorders include Alzheimer's Disease, neurodegenerative diseases, post traumatic stress disorder, and alcohol dependence; and examples of opthamalogical conditions include glaucoma and central serous retinopathy. It has been surprisingly discovered that administration of the same dose of mifepristone can produce widely varying plasma drug concentrations in different patients. For a particular dose of mifepristone, the plasma drug concentration can differ by as much as 800% from one patient to the next. The varied plasma drug concentration can result in some patients not receiving an efficacious dose of mifepristone. For these patients in particular, it is necessary to improve the pharmacokinetics of mifepristone upon administration. Treatment with mifepristone can be further understood by reference to the following commonly-owned application: U.S. application Ser. No. 13/677,465 filed Nov. 15, 2012 entitled "Optimizing Mifepristone Absorption," the disclosure of which is incorporated by reference in its entirety. It is understood that the methods and systems of the present invention may be used in variety of treatments, and are particularly advantageous when used with complex and difficult to manage treatments, such as any therapy that requires dose titration over time. The length of such therapies may extend over a period of weeks, months, a year or many years. Another difficult to manage therapy is chemotherapy, which often involves administration of chemotherapy agents in a treatment regimen over three months or more and require tight adherence that may benefit from symptom tracking. Various conditions, illnesses and therapies, including any of those described herein, can be more effectively managed to provide improved patient outcomes by utilizing the symptom tracking methods and systems described herein.

Given the variability of symptoms experienced in a patient having Cushing's syndrome, as well as the varied responses to medication, use of a symptom tracker system, such as described herein, is particularly suited for tracking symptoms associated with Cushing's Syndrome. It is appreciated however that the symptom tracker System may be used with various other chronic conditions, particularly conditions that can exhibit seemingly unpredictable variability in symptoms and/or responses to medications, including but not limited to various types of inflammation, such as arthritis; disorders of the skin, such as psoriasis; blood, kidney, eye, thyroid, and intestinal disorders (e.g., colitis); allergies; multiple sclerosis; and asthma.

In one aspect, the Symptom Tracking System utilizes an image-based tracking feature that is particularly useful for diagnosis and management of chronic diseases or conditions that exhibit noticeable changes in appearance. In particular Cushing's Syndrome, a pituitary gland disorder often causes increases in facial fat resulting in a rounded facial appearance often referred to as "moon face." In Cushing's Syndrome, prolonged exposure to high levels of the hormone cortisol result in rapid weight gain, particularly in the trunk and face. A common symptom of Cushing's is the growth of fat pads along the collarbone, the back of the neck and the sides of the face resulting in a widened, rounder face. While a hallmark sign of Cushing's, these changes can be difficult to recognize over long periods of time or differentiate from normal weigh gain, particularly if a patient's in-person visits to a clinician are infrequent. Since Cushing's may be caused by various factors (pituitary disorder, response to medications, tumor, or trauma to the pituitary gland), treatments for Cushing's vary and may include surgery and/or medications. In patients where surgery is not suitable, patients typically are treated by medications and their progress is monitored. Maintaining proper levels of cortisol can be challenging, however, and hormone levels and symptoms must be monitored closely to track progress and manage treatment as needed.

In one aspect, any outwardly visible symptoms may be tracked by image-based tracking and optionally analyzed by the system. Typically, the patient obtains images and uploads the images to the symptom tracking system. Obtaining a self-image with a smartphone and uploading by smartphone is a relatively quick and simple way of recording objective data of the patient's facial appearance to help the patient and/or the medical professional track their progress and assess general trends in the patient's condition based on facial appearance. Such images may allow identification of relatively minor physical changes that other physiological measurements may not readily identify. In addition, these changes can be identified by the system without requiring frequent in-person visits to the clinician. Since in Cushing's Syndrome, the patient may experience an increase in size and thickness in fat pads on the sides of their face or on the back of their neck which is disproportionate from regular weight gain, this development can be more readily identified in a progression of photographs than merely from merely tracking weight gain in general, particularly since a patient's weight may fluctuate for a variety of reasons unrelated to the chronic condition (e.g. depression, life changes, injury, etc.) While this image-based feature relates to outwardly visible symptoms observable from an image, it is appreciated that various other symptoms suitable for tracking in accordance with the methods described herein are not necessarily outwardly visible and may be determined from various other means, including but not limited to various types of testing (e.g. blood testing, blood pressure, physical testing/examination, etc.).

This image-based tracking feature assists in diagnosis and tracking of the outward symptoms of Cushing's by comparing images of the subject over time and monitoring the type and magnitude of changes in physical appearance, especially changes in facial appearance. These changes may be difficult to quantity and to distinguish from ordinary changes in weight. The tracking system should be capable of recognizing the patient's face sufficiently to allow comparison between images to identify relatively small changes in facial appearance between images. For example, the system may run a "facial recognition subroutine" that may recognize the imaged face and/or normalize the images to allow direct comparison between images. The images may be obtained by a user at home with an integrated laptop camera or web camera and uploaded onto a server and associated with a user account to allow tracking of the user's symptoms. By comparing a series of images over time, the tracking system can monitor and track subtle changes and general trends that would be difficult to quantify otherwise and assist in monitoring and treatment of the condition. In addition, tracking the symptoms over time allows the patient or medical professional to monitor the progress of the syndrome as well its response to treatment so that treatments can be adjusted as needed to improve patient outcomes.

In one aspect, methods include image-based tracking of symptoms relating to outward physical appearance using a series of images uploaded by the patient over time into the symptom tracking system. In certain aspects, methods of determining changes in facial shape that may be attributable to Cushing's Syndrome include any or all of the following: tracking of changes in facial shape/appearance based on series of images over time; methods for determining increased fat deposits based on comparison between images; methods for normalizing a series of images to allow comparison of features between images; methods for tracking progression of symptoms based on changes in outwardly visible symptoms; methods for prescribing treatment based on history of tracked visual symptoms and past treatment; methods/systems utilizing a "facial recognition routine" to allow comparison between facial images; and a web-based system allowing user to upload images, compare changes between images to determine symptoms and provide tracking history of symptoms to user and/or medical professional.

Management of a chronic condition using a Symptom Tracking System in accordance with aspects of the invention can be further understood by reference to FIG. 1, which illustrates a flow chart of an example symptom tracking system. This system includes a symptom tracking information system provided by the developer of a pharmaceutical used in treatment of the chronic condition in which fields of information are input by a user (typically the patient, although a patient and physician may work together to establish a profile). In this example, the system is accessible online by a patient such that the patient establishes a patient profile in the symptom tracking system maintained by the drug developer and symptom information on the selected symptoms is routinely input by the patient over time. The information is stored by the system and reports based on the data are output to any of the patient, physician or developer upon request, the differing in type and information based on the recipient and/or query. In certain aspects, the system analyzes the symptom information according to one or more algorithms or relationships stored in a processing unit of the system. The relationships or algorithms may be determined by the processing unit based on statistical analysis of the information or may be input by or more entities as they become known, such as through clinical studies. In this example, the information and algorithms are input on a symptom tracking information system maintained by the drug developer, although it is appreciated that the information and algorithms input into the system can be received from various different entities or uploaded automatically from various other information sources.

In one aspect, the management methods and symptom tracking system described herein may incorporate any aspect of the information systems described in U.S. Provisional 61/880,785 filed Sep. 20, 2013, entitled "Systems and Methods of Treatment Using Intervention Determination and Tasking," the entire contents of which are incorporated herein in its entirety.

In another aspect, the system allows for analysis of one or more symptoms over time to determine a trend or certain combination of symptoms for use by the physician in treating the particular patient or to determine statistical information that may be used by the physician or the drug developer to improve treatment regimens. In one aspect, data relating to one or more symptoms entered by a patient may be directly accessible by the treating physician on an as needed basis or may be obtained by the physician from reports produced on a periodic basis or in response to a trigger condition, such as a symptom exceeding a specified range or value relative a baseline. In another aspect, the system may provide the physician with analyzed data, such as a trend of one or more symptoms over time, to assist the physician in making a determination of the patient's condition and/or the efficacy of treatment. In yet another aspect, the system may perform a statistical analysis on the data entered by multiple patients and provide sortable data or provide results from a statistical analysis of the one or more patient symptoms or treatment efficacy in relation to a patient attribute.

FIG. 1 illustrates a flow chart in an example symptom tracking system. The symptom tracking system may include a symptom tracking information system provided and supported by the drug developer or manufacturer and made accessible to the patient(s), physician(s), medical facility or third parties online, such as through a mobile device app or an online portal. The user may input data into the system, for example a patient or caretaker may input symptoms through a computer accessing the online system or through the mobile device or smartphone application. The information is stored in the symptom tracker information system, along with information input by numerous other patients. The information may be associated with various identifiers or attributes (e.g. patient name, physician, condition, treatment, geographical location, etc.) so as to allow further analysis, such as statistical analysis or trend analysis, based on a community or subset of patients. In another aspect, determining community trending or statistics based on geographical location is particularly useful in administrative management of treatment administration by the drug developer, manufacturer, pharmacy, health care administrator and insurer. In some aspects, the physician may input data into the system (not shown). The information may then be output to a user of the information system, shown in dotted line, in the form of reports or various other means, which may take the form of visual displays on computer screens, touchpads, mobile devices, e-mails, written print outs or other means of communicating information to the user. The information may be output directly to the user, such as user input data in summary or timeline form, or the information may be analyzed, such as by an algorithm, statistical or trend analysis, before being output to the user in a report. The output data may include information pertaining to a particular patient or to a patient community, such as information pertaining to a community of patient of which the particular patient is included, or as to any community of patients of which the user requests information. The report may be output periodically or may be output in response to a particular condition of a patient or community, or in response to a query by a user. It should be noted that the information may be output to any user, in many different types or formats by various different means depending on the data and the user.

In one aspect, the system is configured to allow one type of user to contact another type of user. For example, after viewing reported info, the physician may utilize the system to contact the patient, or may input data associated with the patient profile (such as an update in regard to the treatment regimen or a message to the patient). In another aspect, the drug developer or manufacturer may contact the patient directly through the system, such as to provide information regarding the treatment regimen or management of treatment, to schedule a physician follow-up or to provide patient support. This may be performed in response to a report from the system that the patient is in a vulnerable patient population, such as may be based on a noted trend in symptoms or a community trend. Contact with the patient may be performed through the patient profile, such as by a message that appears when the patient logs onto their profile in the system to enter data. The system may be configured to allow one type of user to contact another type or different types of users, such as the drug developer contacting each or any of the patient, the physician and the pharmacy. Such contact may include a report output to the specified user or may further include additional information or instructions.

According to some embodiments, the symptom tracking information system is provided as an online accessible system maintained on a server and/or on a cloud-based systems. A cloud server may be useful for providing information and advanced information process to a variety of different users accessing the device from various different systems. Different types of data may be accessible to different types of user and/or based on where the user is accessing the system. In another aspect, privileges may be used to protect patient data and/or community data. Dependent upon the privileges associated with their roles (e.g., doctors, insurance agents, patients, or third party data analysts or researchers), different participants may be limited to access only a portion of information relating to the images or a subset of the processing tools without compromising the privacy of the patients associated with the patient information.

According to some embodiments, a server and/or cloud-based system includes a data gateway manager to automatically and/or manually transfer information to/from data providers. Such data gateway management may be performed based on a set of rules or policies, which may be configured by an administrator or authorized personnel. In one embodiment, in response to updates to patient information or treatment regimens, the data gateway manager is configured to transmit over a network (e.g., Internet or intranet) the updated information, such as an updated symptom tracking report. In addition, the data gateway manager may further transfer data amongst multiple data providers that are associated with the same entity (e.g., multiple parties associated with one type of user, such as physicians or the drug developer). The gateway manager may comprise a router, a computer, software or any combination of these components.

Figure 2A:
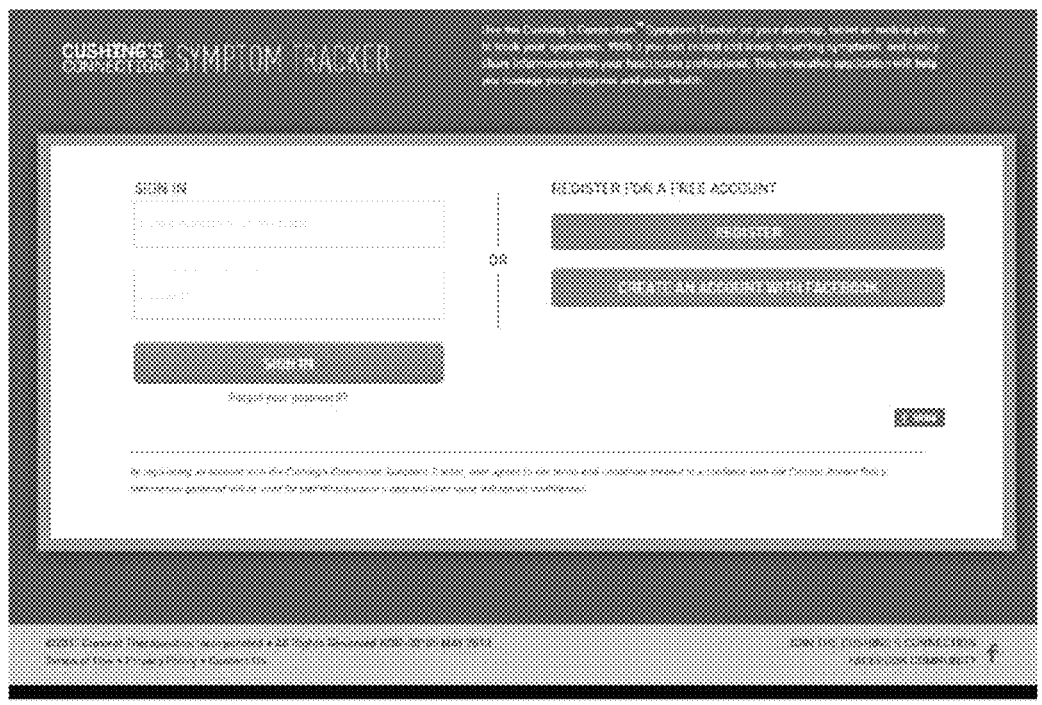
FIGS. 2A-2C illustrate screenshots of an example symptom tracking system for management of a chronic condition relating to establishing a patient profile.
Figure 2B:
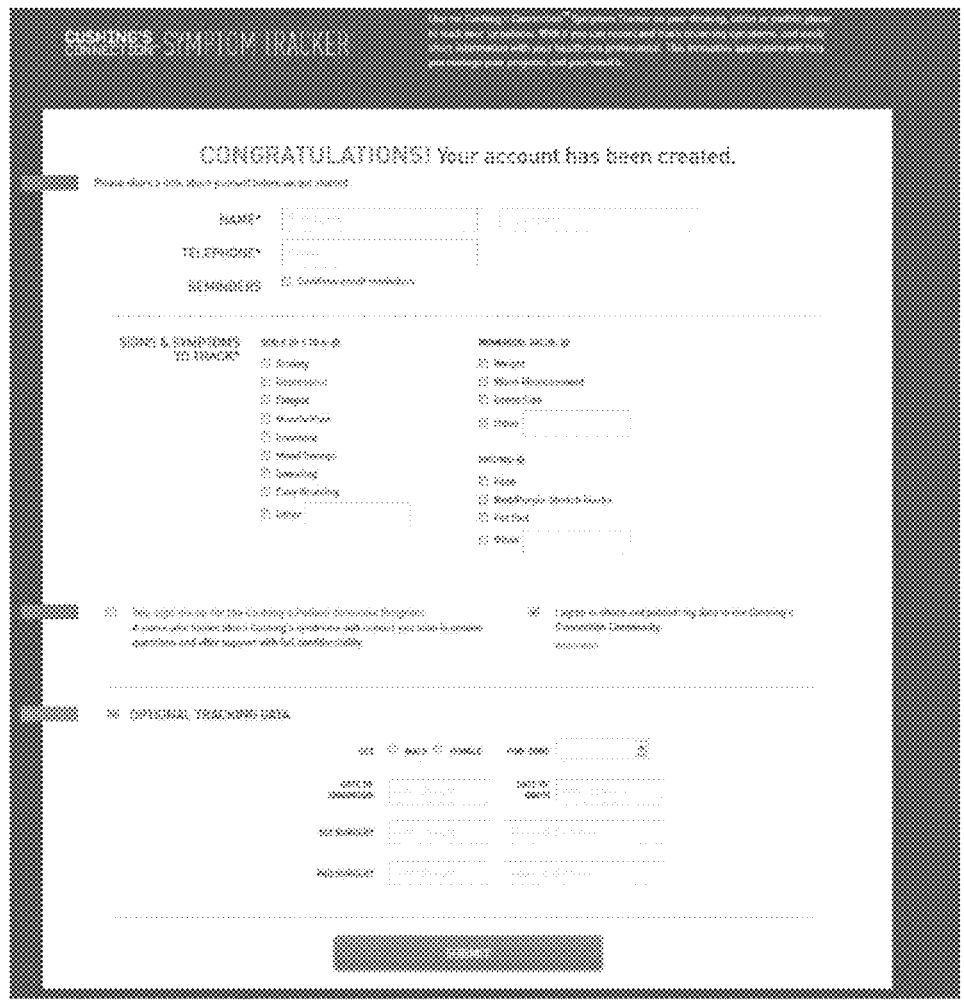
Figure 2C:
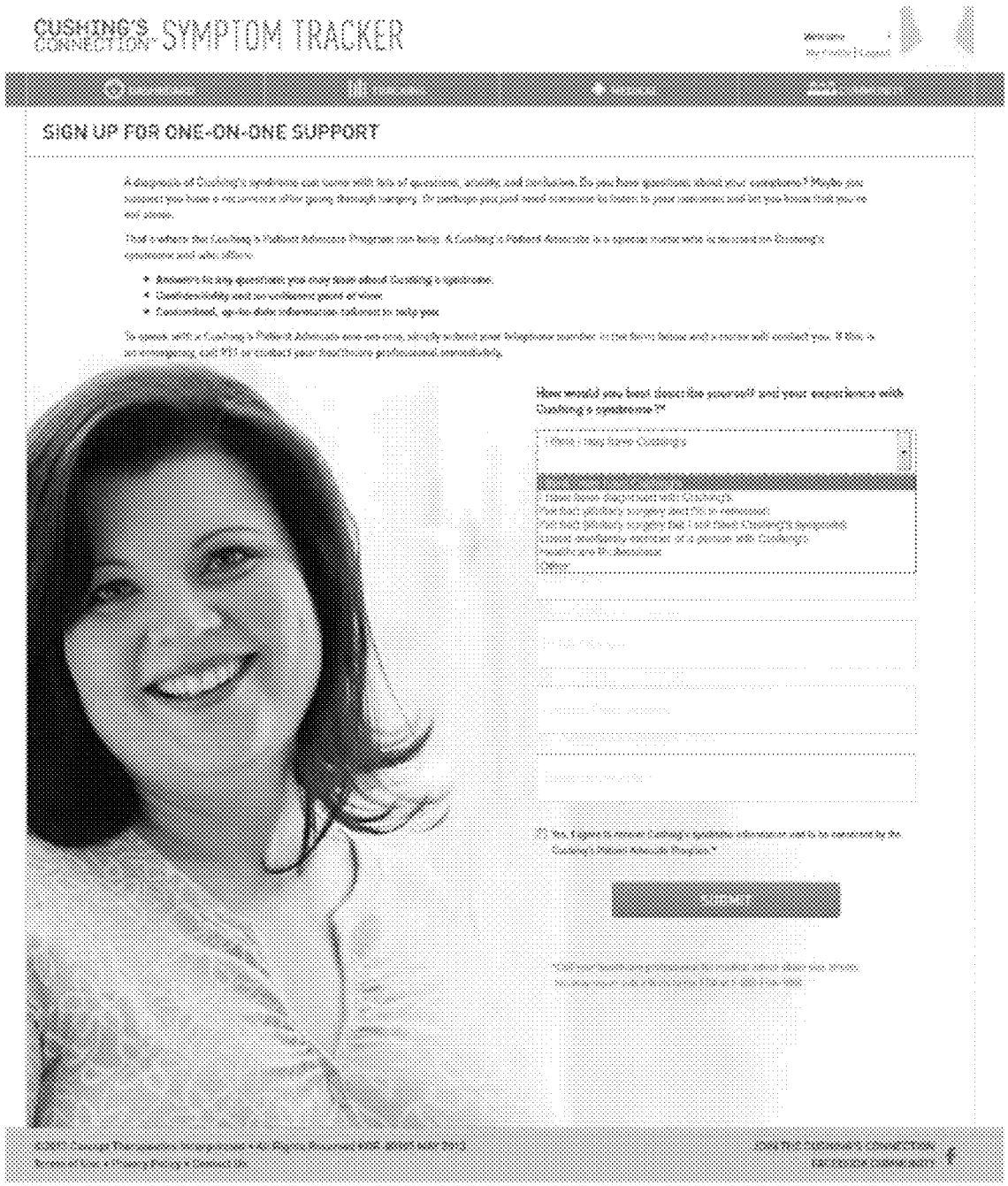

FIGS. 2A-2C illustrate screenshots as would be seen by the patient when accessing the symptom tracker system online to establish a patient profile. As can be seen in FIG. 2A, the account may be linked to an e-mail of the patient, to a Facebook account or facebook support group (e.g. Cushing's Connection). Upon registering, the patient may select what types of symptoms should be tracked, such as shown in FIG. 2B. A physician may assist the patient in determining which symptoms to track or in selecting the symptoms on the patient's profile. The patient may also track various other types of information such as date of diagnosis, dates of surgery and treatment regimen. The more details the patients adds to the profile, the more effectively the patient and/or medical professional can track the patient's symptoms, condition and progress during treatment. When tracking the signed and symptoms, the patient rates each of the signs and symptoms on a scale of 1 to 5.

In one aspect, the signs and symptoms tracking may include tracking of physiological measurements, including but not limited to weight, blood pressure, and waist size. These are physiological measurements that may be obtained by a device used in the patient's home or at a medical facility and automatically uploaded to the patient's profile, or more typically, may be measured by the patient at home and input into the system by the user. In one aspect, the patient is directed to record certain physiological measurements at regular intervals, for example weekly or daily weight measurements obtained at about the same time of day. This improves accuracy of physiological measurements and allows the patient and/or medical professional to more accurately determine trends over periods of time as opposed to normal daily, monthly or seasonal fluctuations. In another aspect, the patient may record subjective attributes of their condition, for example, the patient may record how they are feeling physically (e.g. energetic, tired, or a "normal" baseline) and/or how they are feeling emotionally (e.g. happy, sad, depressed, etc.), which may also correlate with changes in weight or various other physiological measurements.

In another aspect, the system may further provide registration to and/or access to one-on-one support or patient outreach programs, such as shown in FIG. 2C, to further improve patient compliance with the Symptom Tracking System and improve patient outcomes.

Figure 3A:
FIGS. 3A-3C illustrate screenshots of an example symptom tracking system for management of a chronic condition relating to the patient dashboard, profile and facial image information.
Figure 3B:
Figure 3C:
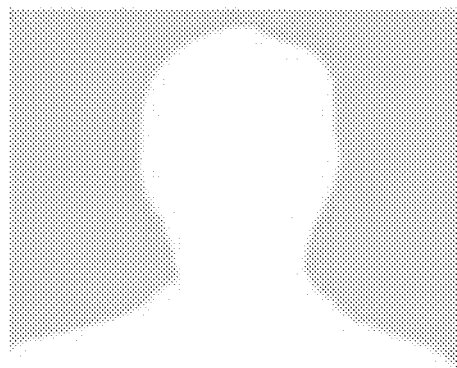
Figure 4:
FIG. 4 illustrates screenshots of an example symptom tracking system for management of a chronic condition relating to selection and entry of symptoms by the patient.
Figure 5A:
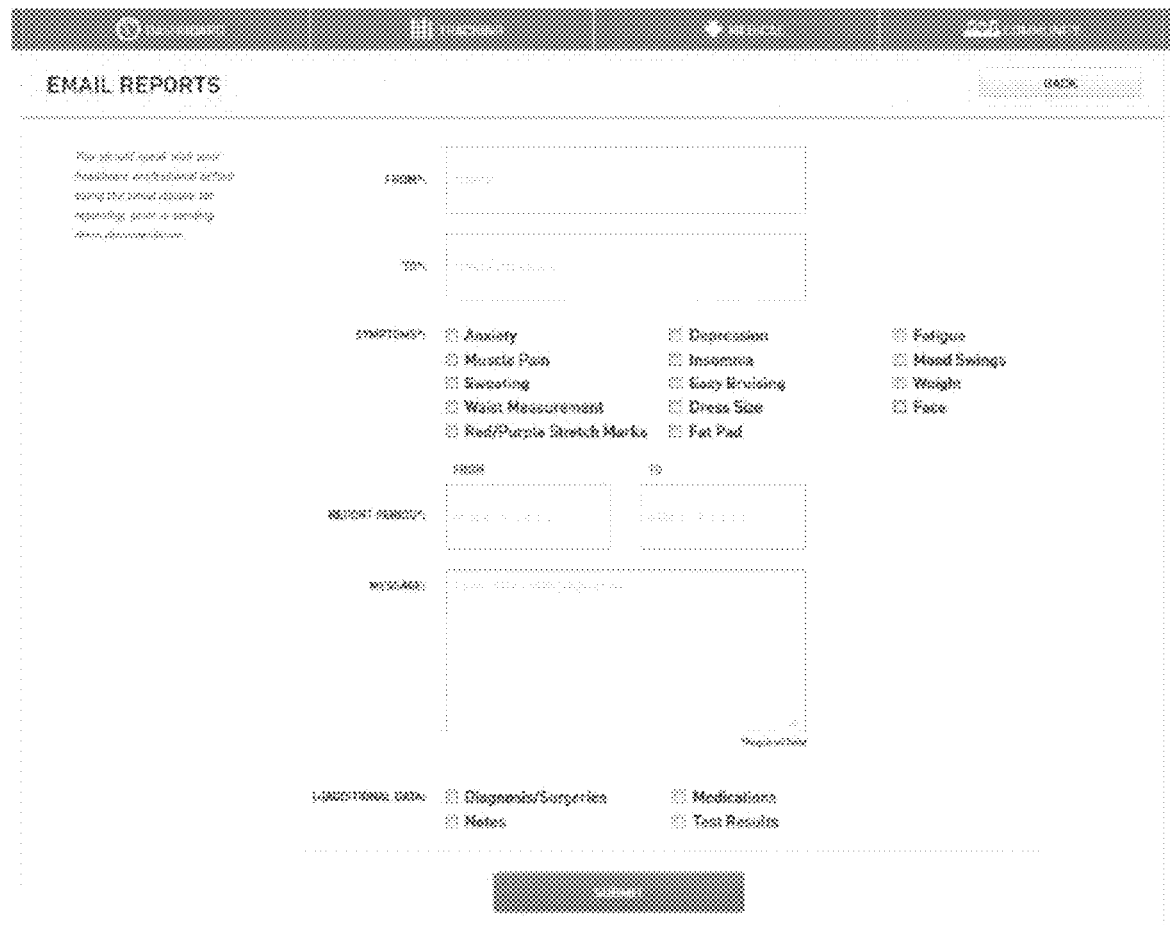
FIGS. 5A-5B illustrate screenshots of an example symptom tracking system for management of a chronic condition relating to reports or alerts regarding tracked symptoms.
Figure 5B:
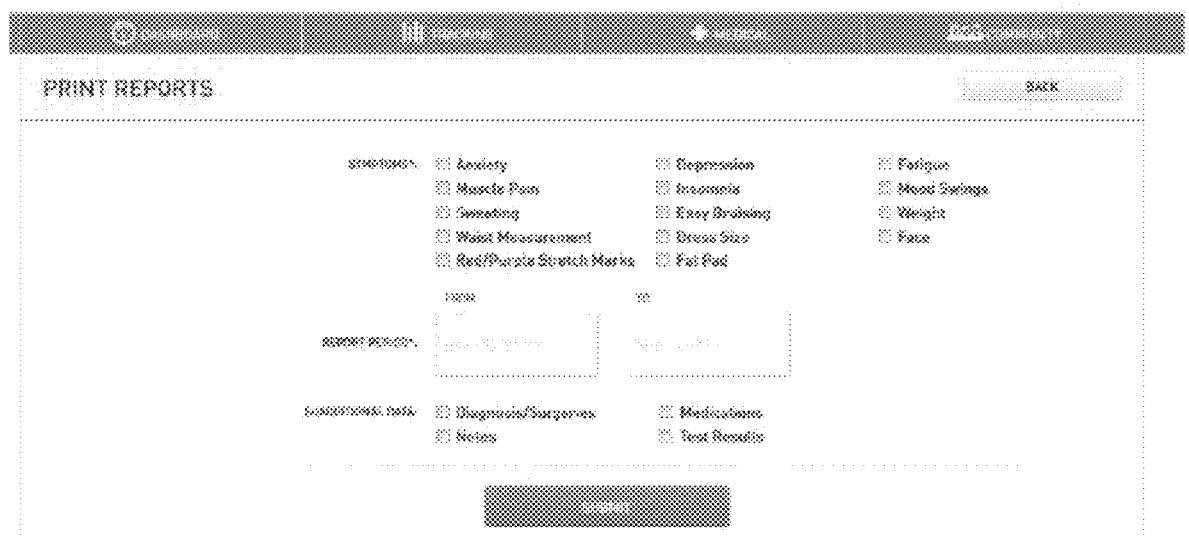
Figure 6A:
Figure 6B:
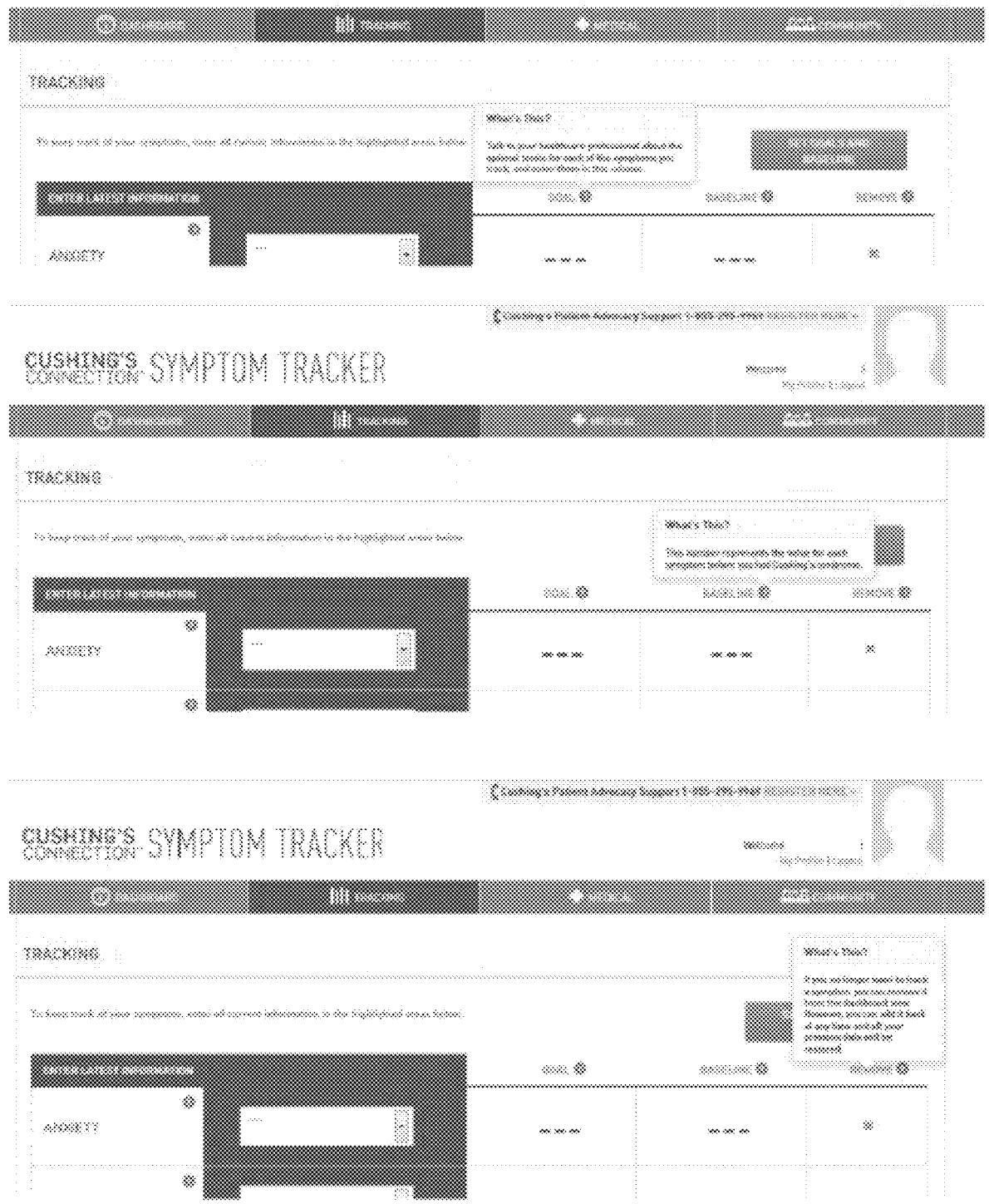
Figure 7A:
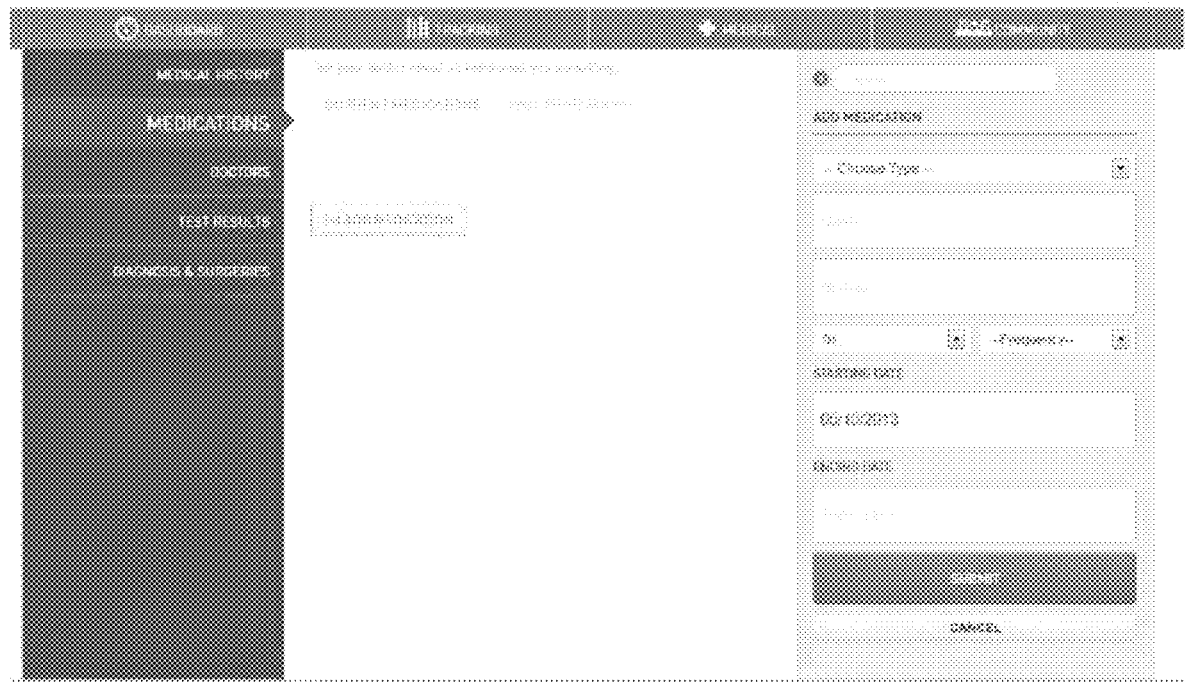
FIGS. 7A-7D illustrate screenshots of an example symptom tracking system for management of a chronic condition relating to entry of patient data to further inform symptom tracking and assessment.
Figure 7B:
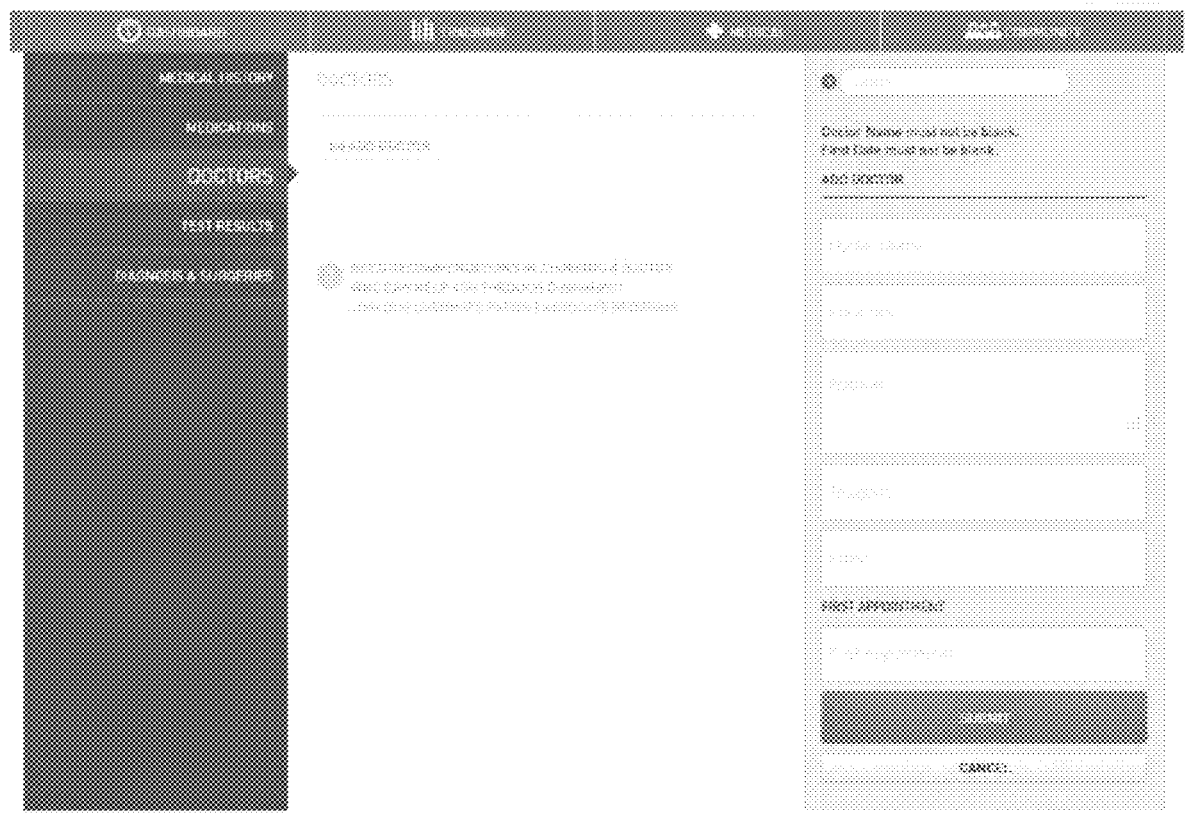
Figure 7C:
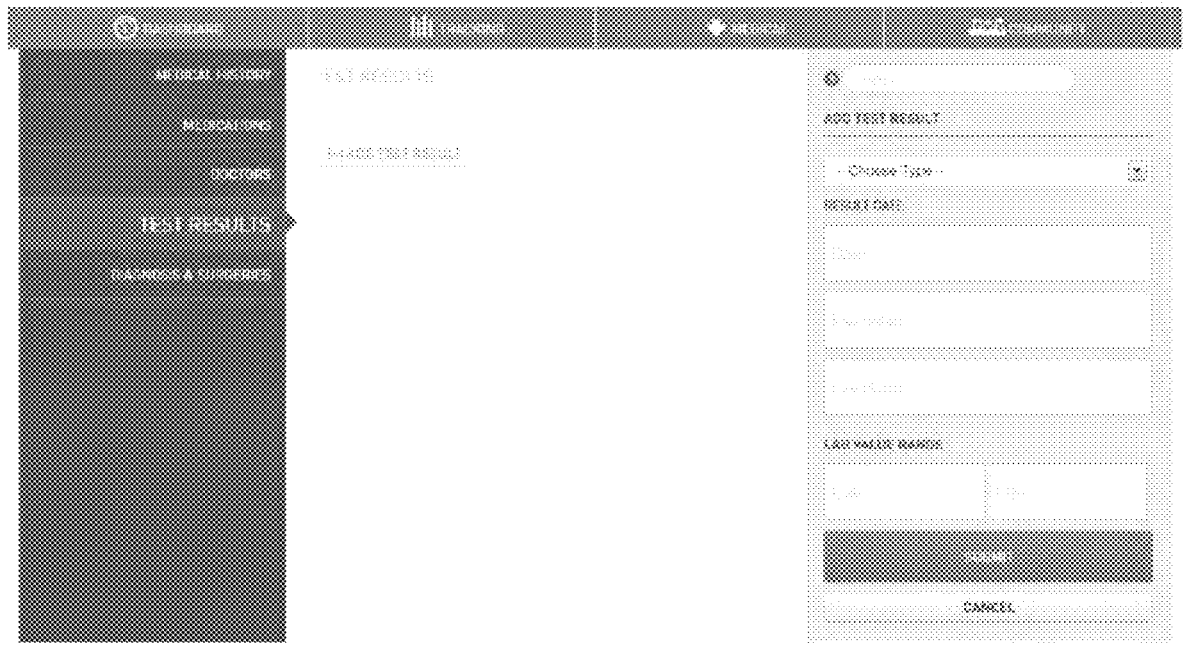
Figure 7D:
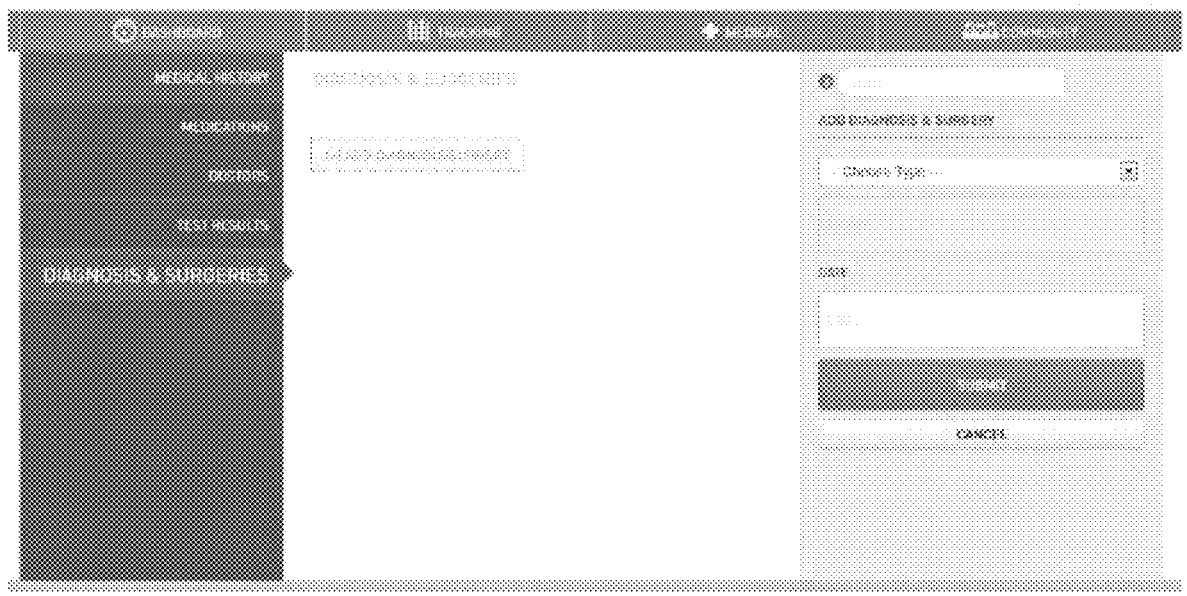
Figure 8:
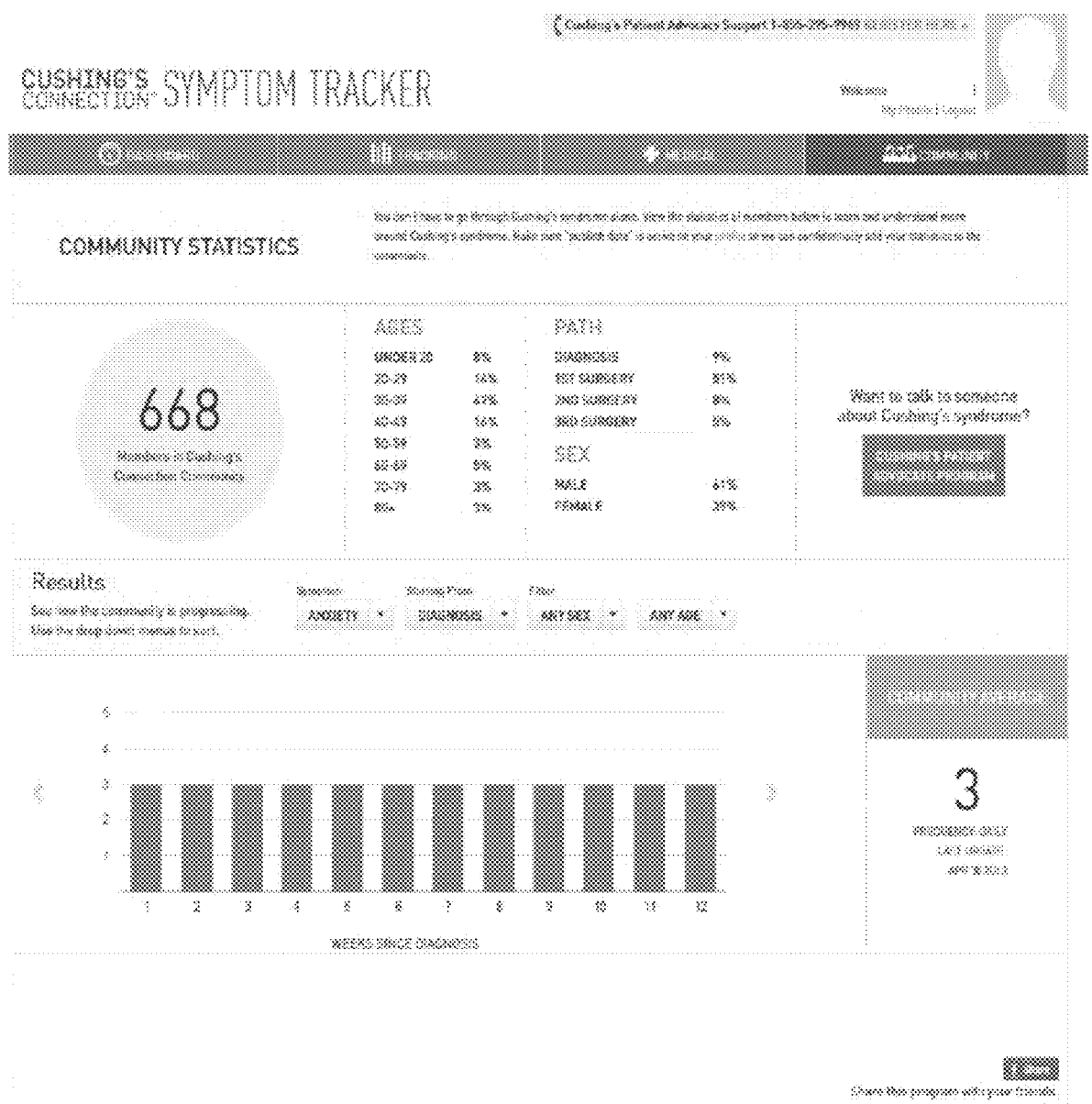
FIG. 8 illustrates a screenshot of a statistical analysis report output by an example symptom tracking system for use in management of various aspects of treatments for chronic conditions.
Figure 9A:
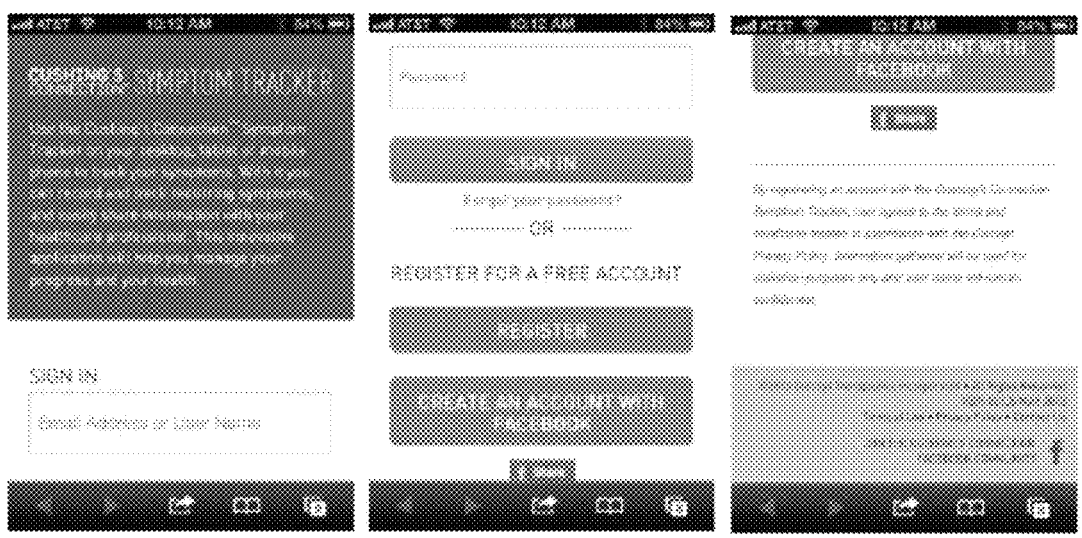
FIGS. 9A-9K illustrate screenshots of an example symptom tracking system as displayed on a patient's smartphone to allow entry and monitoring of data in the system.
Figure 9B:
Figure 9C:
Figure 9D:
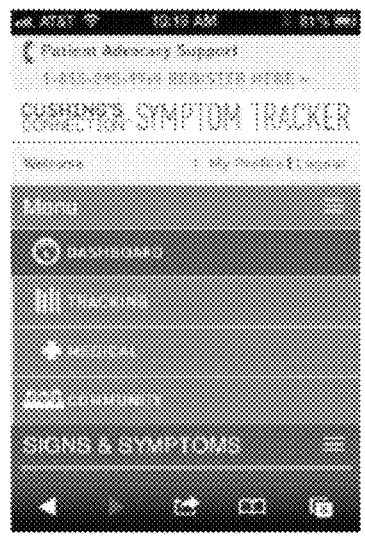
Figure 9E:
Figure 9F:
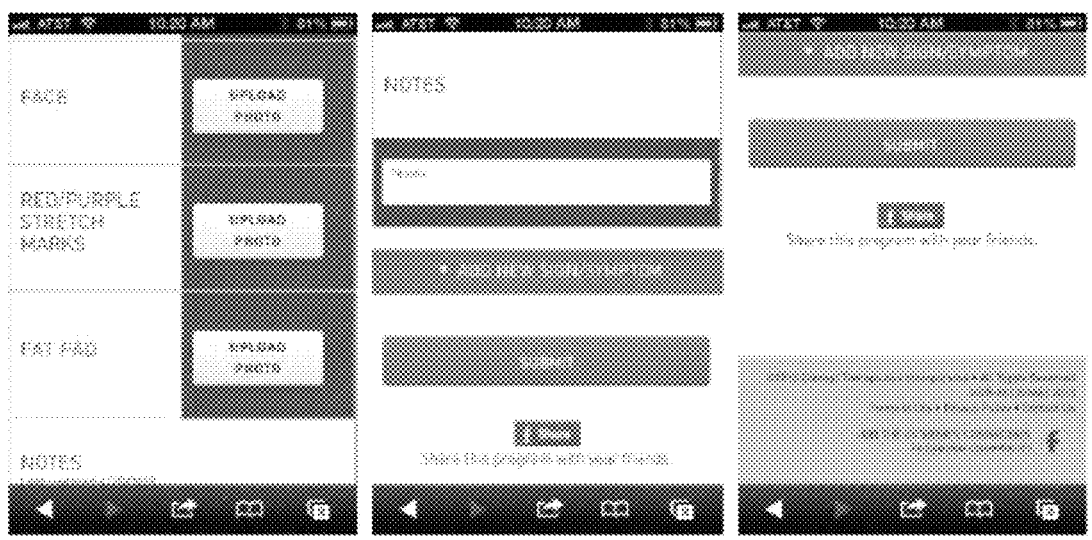
Figure 9G:
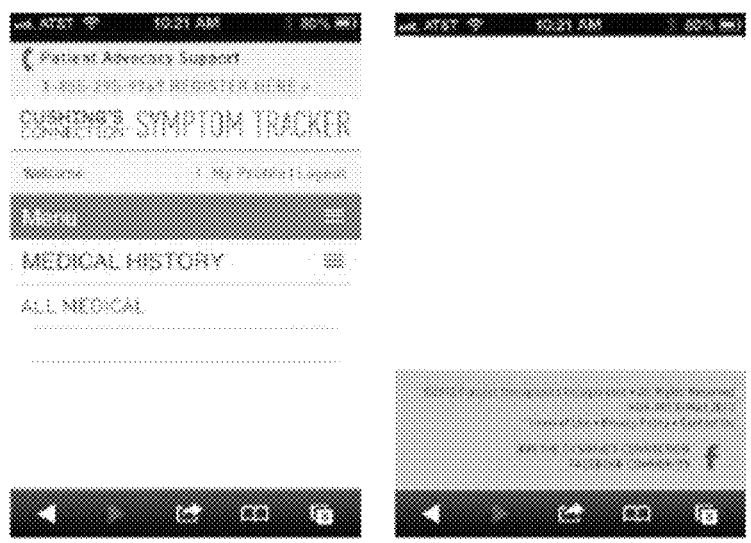
Figure 9H:
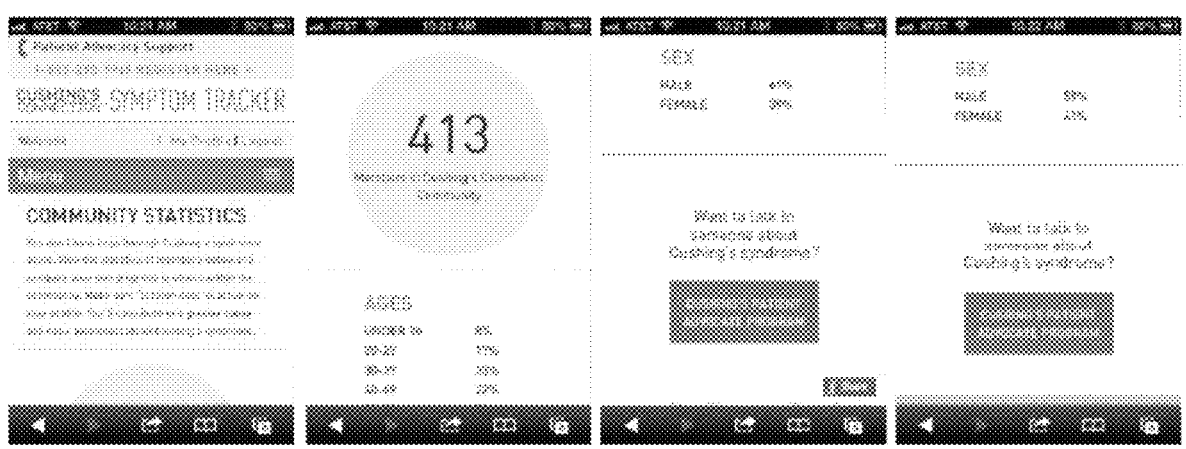
Figure 9I:
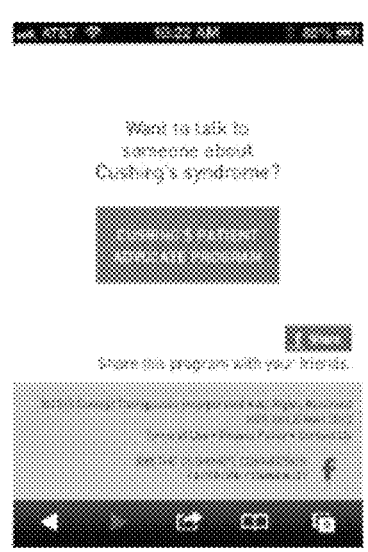
Figure 9J:
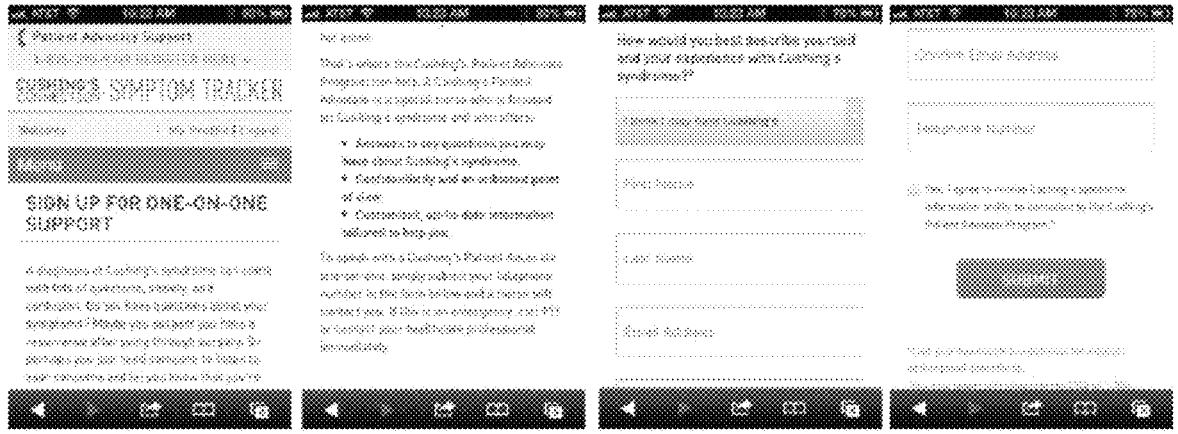
Figure 9K:

In some aspects, the patient may enter various additional attributes that may be useful for monitoring and analysis of the data by the physician and/or in a statistical analysis for use by the drug developer, such as shown in FIG. 3B. In some embodiments, the patient may also set whether to receive notification and reminders as to information regarding treatment and/or their personalized symptom tracking. Since patient's having Cushing's often have gradual changes in facial appearance, such as an increase in fat pad thickness, the patients are encouraged to select facial appearance as a symptom and to record images of the their face over time, such as shown in FIG. 3C. The images can be readily obtained with a smart phone of the patient and uploaded using a smartphone app linked to the symptom tracking system (see screenshots of such a mobile app in FIGS. 9A-9K).

Figure 10:
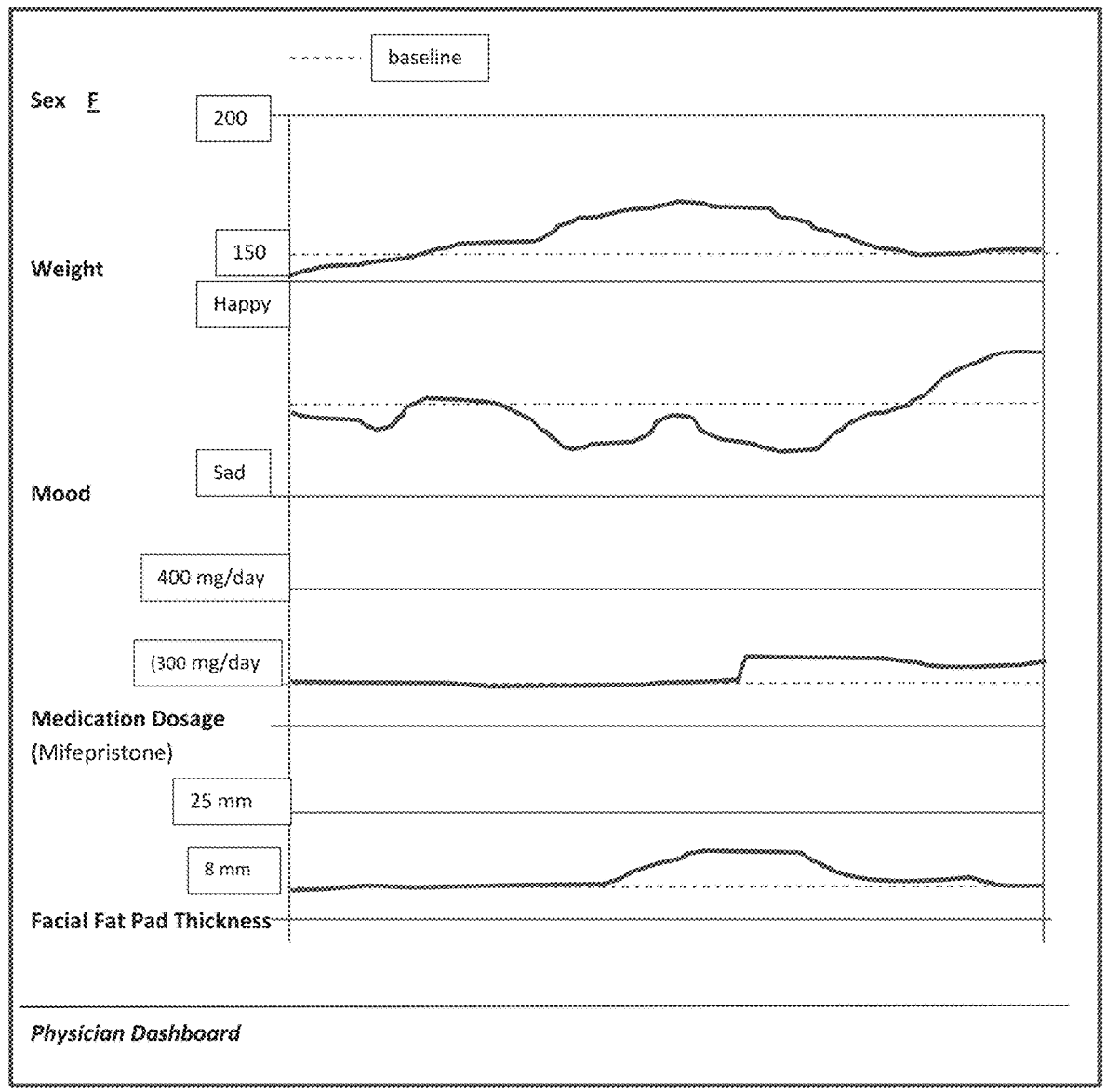
FIG. 10 illustrates an example report output by the example symptom tracking system on a physician dashboard displaying multiple symptoms over time to facilitate monitoring and assessment of the condition and associated treatment.

In one aspect, the images can be later viewed by the patient, physician or drug developer in a format that allows changes in facial dimensions, size and shape to be readily observed by the viewer. For example, the images may be displayed simultaneously in chronological order, such as in the photo timeline display shown in FIG. 11. Such a display format allows the patient and/or physician to more readily recognize changes in facial shape that may be disproportional from normal weight gain. In addition, since weight may fluctuate for a variety of reasons, it may be further useful to track other attributes or possible factors that relate to the one or more selected symptoms but that may also be independent of the chronic condition. For example, by tracking a patient's mood (e.g. anxiety level, depression), it may be determined that a change in weight may correlate more closely an emotional state rather than a poorly regulated hormonal level. Since interactions may be complicated, the reports provided to a patient or the physician may include multiple symptoms and patient attributes displayed simultaneously to assist in determining the possible causes and correlations of the symptoms, such as shown in FIG. 10. These changes are typically assessed by establishing a baseline for each symptom and/or attribute by which to compare the variations in the symptom and/or patient attribute. In some aspects, the patient or physician may establish a goal for a symptom/attribute. While the actual causes of certain symptoms must often be assessed further in patient counseling and/or through further testing (e.g. endocrine or hormonal testing), such reports are particularly advantageous in alerting both the patient and physician to possible interactions between factors or to correlations that would otherwise escape notice. In addition, the continuous monitoring of these symptoms by both the patient and physician using the Symptom Tracking System allows subtle changes to be identified more quickly than would they would otherwise, thereby allowing the physician and patient an opportunity to adjust a regimen or improve patient compliance and prevent relapse of the condition or to reduce the length of a relapse before symptoms escalate.

In another aspect, the factors tracked may be certain compounds in the patient's blood over time for use in diagnosis and/or treatment. Such factors may include: blood glucose measurements, in particular hBalz and OGTT; hormones that provide an overview of the activity of the HP-axis, which may include but are not limited to, ACTH, CRH and DHEA-S; and various proteins, RNA molecules, or other compounds, such as FKBP51, mRNA and GILZ mRNA, which allow the physician to better understand the downstream effects of cortisol activity in the body. It is appreciated that tracking of these factors may be analyzed in isolation, or in combination with various other patient attributes and/or symptoms described herein. For example, tracking of one or more of the above noted compounds in the patient's blood can provide a more comprehensive picture of the patient's state when combined with tracking of the patient's subjective data (e.g. moods, pain), or when combined with image-based monitoring (e.g. changes in the shape or size of the patient's face). By analyzing these seemingly disparate factors, attributes and/or symptoms over a long period of time, trends and associations that may not otherwise be appreciated from periodic patient interviews can be determined. Such associations and trends are particularly useful in difficult to manage treatments, such as those described herein.

In another aspect, the symptom tracking system may employ algorithms to more accurately determine subtle changes in facial dimensions of the patient over time from the multiple images uploaded by the patient. Since certain facial dimensions remain constant (e.g. distance between eyes, distance between eyes and nose), image analysis algorithms can be used to determine facial dimensions of changeable portions of the face (typically the sides of the face) to determine an increase in width of the face over time. This feature allows for early identification of an increase in the fat pads on the sides of the face. Existing facial recognition algorithms can be used to identify the locations of eyes and to measure a distance between the eyes and the sides of the face, as well as the overall height of the face in each of the images. The measurements can be compared between images to determine an overall trend in change of the size, and in particular the width of the face. This trend can also be represented be displayed as a value or as a graph within another type of report, such as that in FIG. 10 so that the physician or patient can be alerted to changes in facial shape without actually viewing the facial images.

Figure 11:
FIG. 11 illustrates an example report output by the example symptom tracking system on a physician dashboard displaying facial images over time to facilitate monitoring and assessment of facial appearance symptoms associated with the condition.
Figure 12:
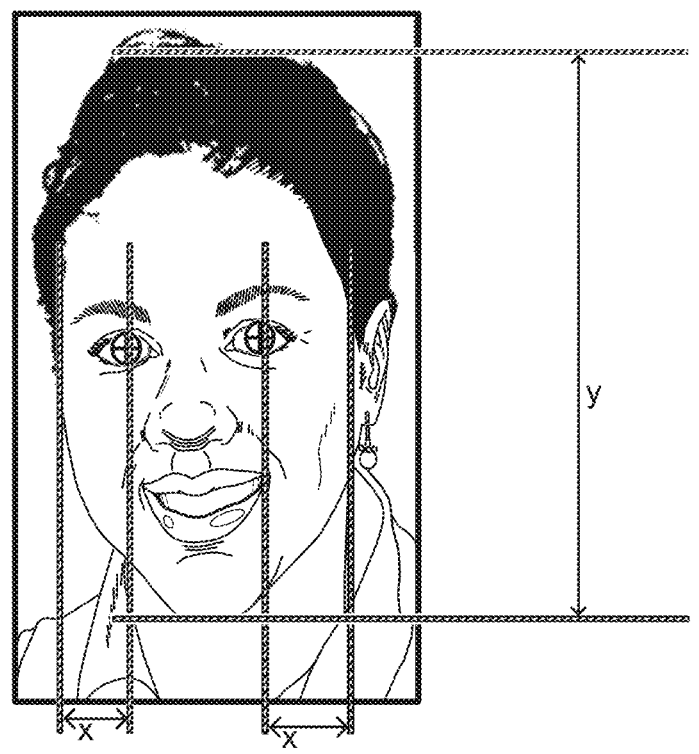
FIG. 12 illustrates an example of an automated analysis of the facial systems to determine changes in facial dimensions or shape over time to facilitate monitoring and assessment of facial appearance symptoms associated with the condition.
Figure 12:
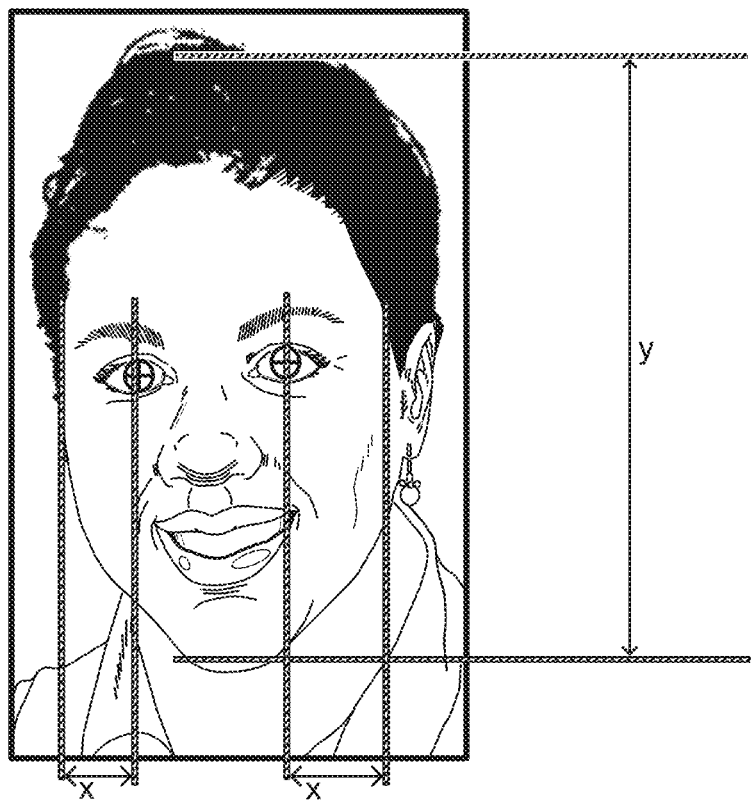

In another aspect, various symptoms, attributes and factors, such as those displayed in the reports in FIGS. 10 and 11, can be assigned a numerical value within an algorithm such that the system could produce an alert to an impending relapse without requiring the patient or physician to actually view the symptom or attribute data in advance. In some aspects, the system may alert the patient or physician to review one or more types of reports in response to a determination that any of the symptoms or patient attributes input by the patient exceed a certain threshold value or range of values (e.g. +/−10% of the baseline value). Advantageously, the system may allow the user, whether the patient, physician or drug developer, to customize a report by selecting which symptoms, attributes or combinations thereof, are desired to be tracked, viewed or analyzed. In some embodiments, the system may analyze the patient attributes and symptoms and determine which are statistically relevant and outputs such attributes/symptoms to the user.

Figure 13:
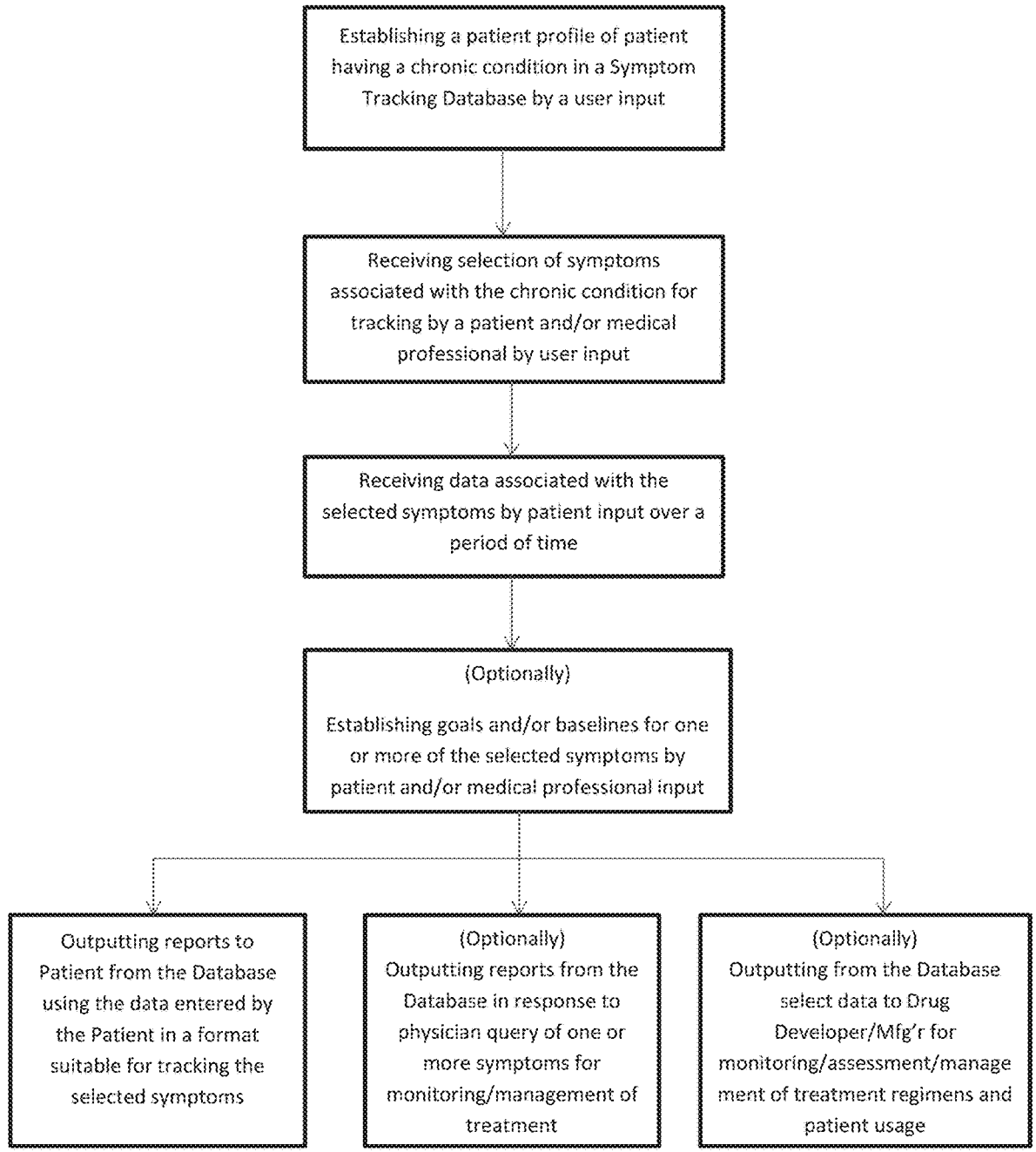
FIG. 13 illustrates an example method using a symptom tracking system in accordance with embodiments of the invention.

FIGS. 13-18 describe various methods by which a chronic condition or associated treatment can be managed or by which production/dissemination of drug information can be managed. FIG. 13 describes a method of management treatment including: establishing a patient profile of a patient having a chronic condition in a symptom tracking database by a user input; receiving selection of symptoms associated with the chronic condition for tracking by a patient and/or medical professional by user input; receiving data associated with the selected symptoms by the patient input over a period of time; optionally, establishing goals and/or baselines for one or more of the selected symptoms by patient and/or medical professional input; outputting reports to patient from the database using the data entered by the patient in a format suitable for tracking the selected symptoms; optionally, outputting reports from the database in response to physician query of one or more symptoms for monitoring or management of treatment; and optionally, outputting from the database select data to a drug developer or drug manufacturer for monitoring, assessment, or management of treatment regimens and patient usage.

Figure 14:
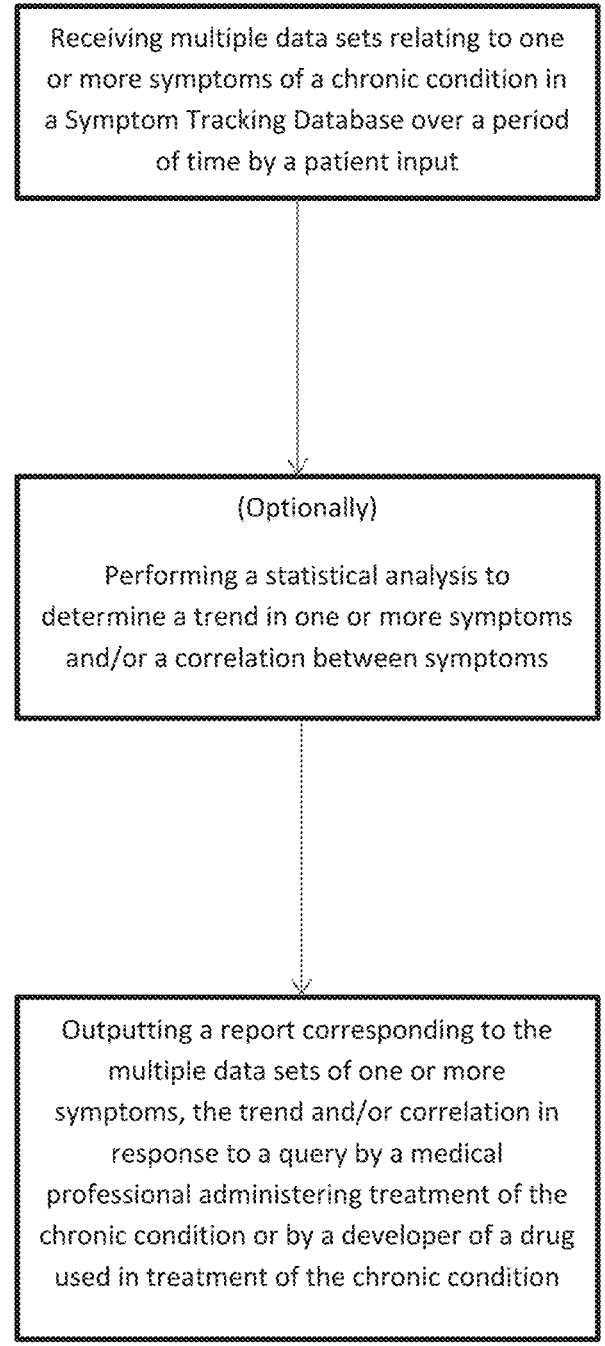
FIG. 14 illustrates an example method using a symptom tracking system in accordance with embodiments of the invention.

FIG. 14 describes a method of treatment management including steps of: receiving multiple data sets relating to one or more symptoms of a chronic condition in a symptom tracking information system over a period of time by a patient input; optionally, performing a statistical analysis to determine a trend in one or more symptoms and/or a correlation between symptoms; and outputting a report corresponding to the multiple data sets of one or more symptoms, the trend and/or correlation in response to a query by a medical professional administering treatment of the chronic condition or by a developer of a drug used in treatment of the chronic condition.

Figure 15:
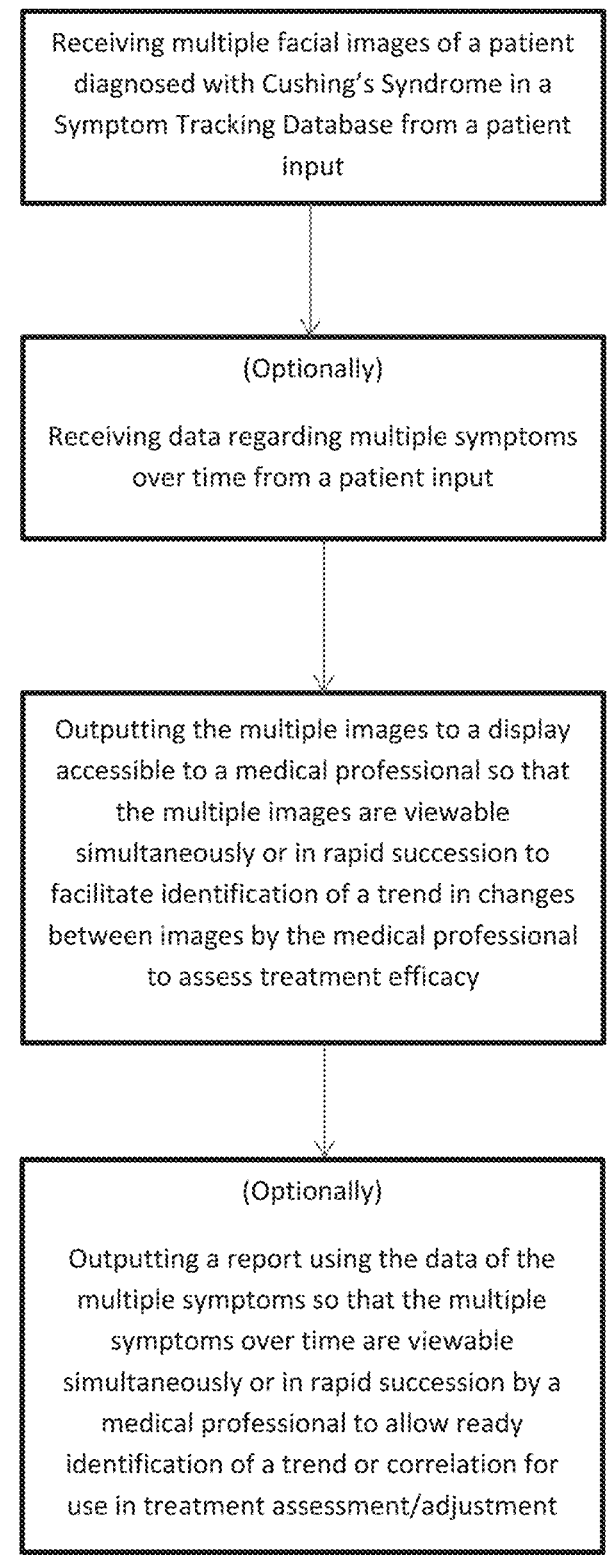
FIG. 15 illustrates an example method using a symptom tracking system in accordance with embodiments of the invention.

FIG. 15 describes a method of treatment management including steps of: receiving multiple facial images of a patient diagnosed with Cushing's Syndrome in a symptom tracking information system from a patient input; optionally, receiving data regarding multiple symptoms over time from a patient input, outputting the multiple images to a display accessible to a medical professional so that the multiple images are viewable simultaneously or in rapid succession to facilitate identification of a trend in changes between images by the medical professional to assess treatment efficacy; and optionally, outputting a report using the data of the multiple symptoms so that the multiple symptoms over time are viewable simultaneously or in rapid succession by a medical professional to allow ready identification of a trend or correlation for use in treatment assessment/adjustment. In another aspect, a method of treatment management may include steps of: receiving data regarding multiple symptoms over time from a patient input; and outputting a report using the data of the multiple symptoms so that the multiple symptoms over time are viewable simultaneously or in rapid succession by a medical professional to allow ready identification of a trend or correlation for use in treatment assessment/adjustment.

Figure 16:
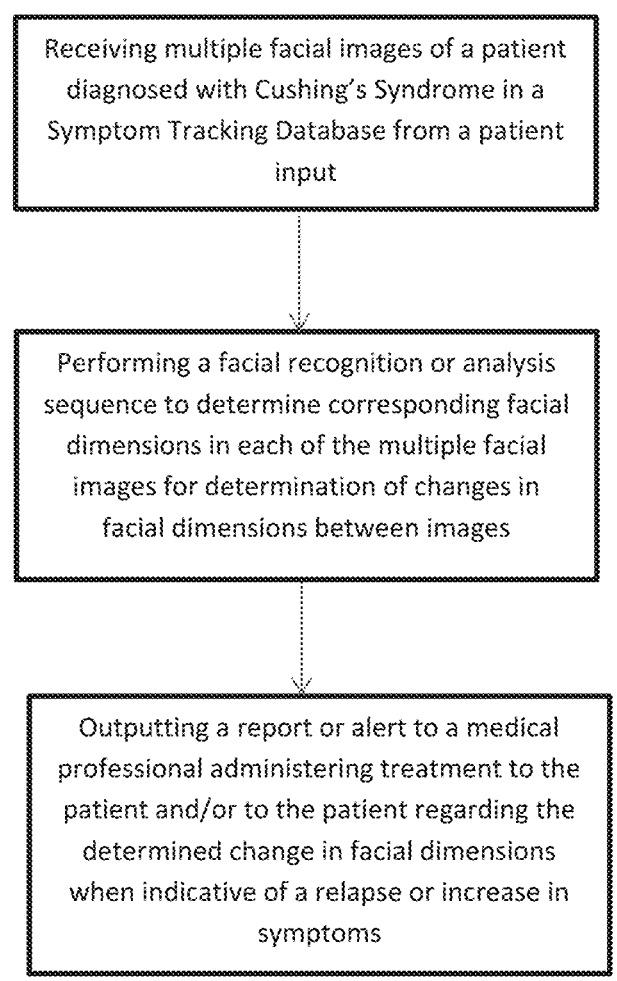
FIG. 16 illustrates an example method using a symptom tracking system in accordance with embodiments of the invention.

FIG. 16 describes a method of treatment management including steps of: receiving multiple facial images of a patient diagnosed with Cushing's Syndrome in a symptom tracking information system from a patient input; performing a facial recognition or analysis sequence to determine corresponding facial dimensions in each of the multiple facial images for determination of changes in facial dimensions between images; and outputting a report or alert to a medical professional administering treatment to the patient and/or to the patient regarding the determined change in facial dimensions when indicative of a relapse or increase in symptoms.

In certain embodiments, the system may further analyze the tracked symptoms and attributes using algorithms input by a user, medical professional, or drug developer. Such algorithms may incorporate relationship or information obtained through clinical studies or may relate to various other concerns, such as various drug supply or administrative processes. Examples of information that may be utilized within such systems include drug information relating to the drug treatment of concern. For example, studies indicate that in administration of mifepristone, plasma levels within the patient drives the drug response. By including this relationship within an algorithm of the system, the system may identify attributes, symptoms, or combinations thereof that correspond with insufficient plasma levels. Such factors may relate to insufficient titration, low dosages, patient attributes, age, diet, through various interactions that may be undetermined. Utilizing the system to store, relate and analyze such factors, however, allows a user to monitor and track various factors and symptoms and intervene as needed to ensure appropriate plasma levels are maintained and facilitate optimized treatment outcomes. Advantageously, the system may provide these benefits even without identifying the relationship to plasma levels or that the plasma level was the factor at issue. This relationship demonstrates some of the complexities and challenges associated with managing treatment of a chronic condition utilizing administration of a drug, particularly in vulnerable patient sub-populations.

Patients utilizing mifepristone to treat medical conditions require intensive follow-up to achieve optimal care and resolution of symptoms, which can lead to variable patient outcomes. Patients in which symptom tracking may be used to improve treatment can be difficult to identify before treatment is either discontinued by the patient or by the physician. For various reasons, such as poor patient compliance, reduced response to prescribed treatment, or influence of external aggravating factors, symptoms may worsen or frequent relapses may occur leading to discontinued treatment. By tracking patient symptoms, the methods described herein allows the physician, as well as the patient, to take a more active role treatment before relapse occurs, which may in turn, improve patient compliance, treatment efficacy and assist in identifying aggravating factors before significant worsening of symptoms occurs.

In some embodiments, the system may utilize any number of algorithms to determine statistical relevance of one or more attributes and symptoms to a result, the result being associated with a relapse. By applying statistical analysis, the system can determine that a relationship is caused by something other than mere random chance so as to determine if the field of information or combination of fields is statistically significant to the desired result. The analysis provides a "p-value" representing the probability that the results is attributable to random chance. In general, a 5% or lower p-value is considered to be statistically significant, although the threshold of significance and desired confidence level may be selected or varied as desired to facilitate a desired result or preventing a relapse or improve treatment approaches.

In some embodiments, the system may utilize an algorithm that applies a known or predicted association between one or more fields and a result that is input by a user or included in a system update. Such algorithms may be determined periodically as associations are identified through clinical studies or otherwise. In some embodiments, the system may apply statistical analysis to determine associations between one or more fields and a result in addition to applying an algorithm input into the system such that the statistical analysis of various fields of information can be reassessed as various other associations are identified over time. These features provide further improvements as ever more complex interactions between the fields of information can be identified and alerts or reports outputted as need to inhibit or reduce adverse effects associated with such interactions and prevent relapse.

While much has been described with respect to analysis and output of data in regard to a particular patient for management of individual patients, these and similar aspects described above may also be applied to collection of symptom data in regard to patient populations, which is particularly advantageous for managing treatment regimens by patient population, which includes various administrative considerations. For example, the symptom tracking system may analyze symptom information from various populations to project or predict a response or to project when a patient may be having a recurrence. In one example regarding response to medication: by breaking patients into a dosing cohort (1 tablet/day to 4 tablets per day), one could then see rate of change in symptoms of themselves versus their and other cohorts, which can be an important tool to the physician in managing treatment. In another aspect, one could also see how nearly all aspects discussed herein here could be compared with others. Anytime one calculates a slope (change in a symptom/measure over time) in regard to an attribute, factor or symptoms, then one could break the information into cohorts, to compare and provide evidence/information to physicians and patients. These aspects would be useful to manage treatment of patient communities by determining a subset of specific cohorts where patients are in disease progression.

While the examples described above are illustrative of some of the basic concepts described herein, it is appreciated that these advantages extend to risk factors and interactions between risk factors that are far more complex, which conventional treatment methods fail to recognize or address and might otherwise prevent a number of patients from receiving optimal treatment. The above described embodiments have been described in some detail for clarity of understanding and by way of example, a variety of adaptations, modifications, and changes will be obvious to those of skill in the art. Hence, the scope of the present invention is limited solely by the appended claims.

What is claimed is:

1. A method for treating a chronic disease or disorder in which patients suffering said chronic disease or disorder exhibit an outwardly visible symptom, wherein said outwardly visible symptom comprises a facial dimension, the method comprising:
   receiving a first image of the patient on a server; receiving a second image of the patient on a server, wherein the second image is captured subsequent to the capture of the first image;
   measuring a facial dimension in each of said first and said second images to provide a baseline measurement and a second measurement, respectively, of said facial dimension;
   comparing the baseline measurement from the first image and second measurement from the second image using a processor;
   determining a change in the facial dimension by determining a distance between an eye and another facial feature; calculating a slope by dividing the change between said facial dimension measurements of at least two facial images of the plurality by the duration of time between said measurements of the two facial images of the plurality; and
   determining a change or trend of change of a facial dimension based on the calculated slope; and
   determining a course of treatment in response to said determined change of the facial dimension.

2. The method of claim 1, wherein the server is accessible online such that the first image and the second image are uploaded by the patient to the server and assigning a task to the intended recipient.

3. The method of claim 1, further comprising:
   receiving a plurality of images captured sequentially over a monitoring period;
   measuring said outwardly visible symptom in each of said plurality of images;
   providing a plurality of facial dimension measurements obtained from said measuring; and comparing at least one of said plurality of facial dimension measurements with another of the plurality of facial dimension measurements, and determining a trend associated with the change in the facial dimension during said monitoring period, wherein the course of treatment is determined in response to the determined trend associated with the change in the symptom facial dimension.

4. The method of claim 1, wherein the facial dimension comprises a facial size determined with respect to one of the patient's eyes, the patient's chin, the top of the patient's head, a side of the patient's face, or other facial feature.

5. The method of claim 4, wherein the chronic disorder is Cushing's Syndrome.

6. A system for treatment of a chronic disease or disorder exhibiting a change in an outwardly visible symptom in a patient, wherein said outwardly visible symptom comprises a facial dimension, the system comprising:

one or more image capture devices adapted for capturing a plurality of facial images of the patient sequentially during a monitoring period;

a server configured for receiving and storing the plurality of facial images of the patient in an information system; and a processor configured for:

measuring a facial dimension of a patient in each of said plurality of facial images;

providing a plurality of facial dimension measurements obtained from said plurality of facial images;

comparing the plurality of facial dimension measurements;

determining a change or a trend of change of the facial dimension by determining a distance between an eye and another facial feature; calculating a slope by dividing the change between said facial dimension measurements of at least two facial images of the plurality by the duration of time between said measurements of the two facial images of the plurality; and determining a change or trend of change of a facial dimension based on the calculated slope; and determining a course of treatment in response to the determined change or trend of the facial dimension.

7. The system of claim 6, further comprising:

a patient input for receiving images obtained by the one or more image capture devices from the patient; and a physician input for receiving patient treatment information used in determining the course of treatment.

8. The system of claim 6, wherein the server is accessible online such that the plurality of facial images are uploadable by the patient through the internet and the plurality of facial images are accessible by the physician through the internet.

9. A method for assessing efficacy of a treatment of a chronic disease or disorder in which patients suffering said chronic disease or disorder exhibit an outwardly visible symptom, wherein said outwardly visible symptom comprises a facial dimension, the method comprising:

receiving multiple facial images of a patient diagnosed with the chronic disease or disorder in a symptom tracking information system from a patient input, said symptom tracking information system comprising an image capture device, a server, and a processor, said multiple facial images being obtained sequentially during a monitoring period;

measuring a facial dimension in each of said multiple facial images;

comparing said facial dimension measurements;

determining a change or a trend of change of the facial dimension during said monitoring period by determining a distance between an eye and another facial feature; calculating a slope by dividing the change between said facial dimension measurements of at least two facial images of the plurality by the duration of time between said measurements of the two facial images of the plurality; and determining a change or trend of change of a facial dimension based on the calculated slope;

providing said facial dimension measurements and said determined changes or trends for outputting; and outputting the multiple facial images, said multiple facial dimension measurements, and said change or trend determinations to a display accessible to a medical professional so that the multiple facial images and the multiple facial dimension measurements are viewable simultaneously or in rapid succession, thereby to facilitate identification of a trend in changes between the facial images and the facial dimension measurements by the medical professional and to facilitate assessment of treatment efficacy.

10. The method of claim 9, further comprising outputting a report for use in treatment assessment, treatment adjustment, or both.

11. The method of claim 9, further comprising outputting a report or alert to a medical professional administering treatment to the patient and/or to the patient regarding the determined change in facial dimension when indicative of a relapse or increase in symptoms.

12. The method of claim 9, wherein the chronic disease or disorder comprises an endocrine disorder and wherein administering treatment comprises modifying a drug regimen.

13. The method of claim 9 wherein the chronic disease or disorder comprises Cushing's Syndrome and the drug comprises mifepristone.

14. The method of claim 9, wherein the chronic disease or disorder is an endocrine disorder, the one or more symptoms comprises any of weight, a fat pad thickness, a body composition, an increase in facial width, a skin discoloration or any combination thereof and the drug is mifepristone.

15. The method of claim 9, further comprising receiving symptom data pertaining to one or more further symptoms of the chronic disease or disorder from a plurality of patients, and:

breaking said symptom data from the plurality of patients into cohorts; and then reporting information relating to a particular cohort to the physician(s) and/or the patient(s) to improve management of treatment.

16. The method of claim 15, further comprising:

analyzing the facial dimension measurements from the plurality of patients to determine a trend in a particular cohort of patients, said cohort of patients being a subset of patients of the plurality of patients that are identified as exhibiting disease progression based on the symptom data regarding the patients;

wherein the report comprises information relating to a trend in the cohort.

17. The method of claim 15, wherein the one or more symptoms comprises two or more symptoms and the report comprises displaying information based on the received symptom data in conjunction with one or more attributes of the patient and/or one or more factors associated with the patient.

18. The method of claim 17, wherein the attributes comprise any of an age, a gender, a duration of treatment, a date of diagnosis, and a treatment regimen.

19. The method of claim 17, wherein the one or more factors comprise one or more compounds measured by blood testing.

20. The method of claim 19, wherein the compounds comprise any of blood glucose measurements, hormone levels, proteins, RNA molecules or any combination thereof.

21. The method of claim 15, wherein the symptoms comprise a test result, including any or all of a physiological measurement, analyte testing, chemical and compound testing.

* * * * *